(12) United States Patent
Kayan

(10) Patent No.: US 6,436,118 B1
(45) Date of Patent: Aug. 20, 2002

(54) IMA DISSECTION DEVICE

(75) Inventor: Helmut Kayan, Redwood City, CA (US)

(73) Assignee: General Surgical Innovations, Inc., Norwalk, CT (US)

(*) Notice: Subject to any disclaimer, the term of this patent is extended or adjusted under 35 U.S.C. 154(b) by 0 days.

(21) Appl. No.: 09/512,934

(22) Filed: Feb. 25, 2000

(51) Int. Cl.⁷ .............................................. A61M 29/00
(52) U.S. Cl. ...................................... 606/192; 606/190
(58) Field of Search .............................. 606/192, 190, 606/108, 194–198; 604/101.01, 101.02, 101.03

(56) References Cited

U.S. PATENT DOCUMENTS

| 4,779,611 A | 10/1988 | Grooters et al. ............... 128/4 |
| 5,601,589 A | 2/1997 | Fogarty et al. ............. 606/192 |
| 5,607,443 A | 3/1997 | Kieturakis et al. .......... 606/192 |
| 5,690,668 A | 11/1997 | Fogarty et al. ............. 606/192 |
| 5,730,757 A | 3/1998 | Benetti et al. .............. 606/198 |
| 5,755,682 A | 5/1998 | Knudson et al. ............... 604/8 |
| 5,758,663 A | 6/1998 | Wilk et al. .................. 128/898 |
| 5,762,604 A | * 6/1998 | Kieturakis ................... 606/190 |
| 5,797,946 A | 8/1998 | Chin .......................... 606/190 |
| 5,797,947 A | 8/1998 | Mollenauer ................. 606/192 |

* cited by examiner

Primary Examiner—Kevin T. Truong

(57) ABSTRACT

A dissection device for dissecting tissue from an elongate structure in a body is disclosed. The device comprises an elongate tubular member such as a cannula or other hollow tube and an inflatable elongate tubular balloon coupled to the elongate tubular member. The device further comprises device for connecting the elongate tubular balloon to an inflation source to inflate the elongate tubular balloon and device for deflating the elongate tubular balloon such as by a deflation valve. The elongate tubular balloon typically has multiple cylindrical chambers, is inverted during its uninflated state and everts during use.

62 Claims, 14 Drawing Sheets

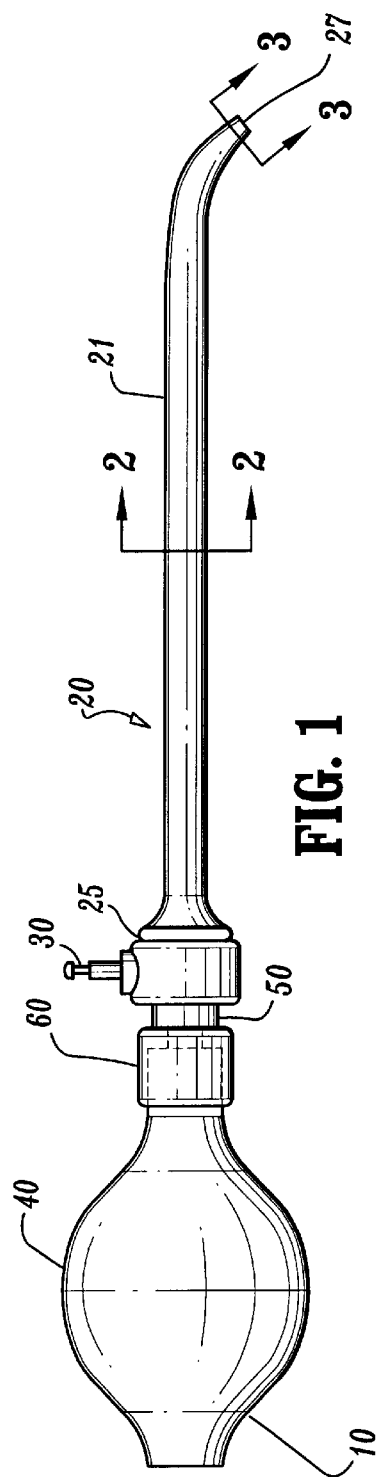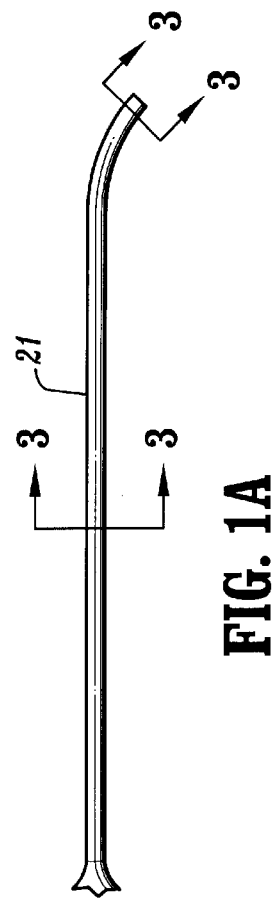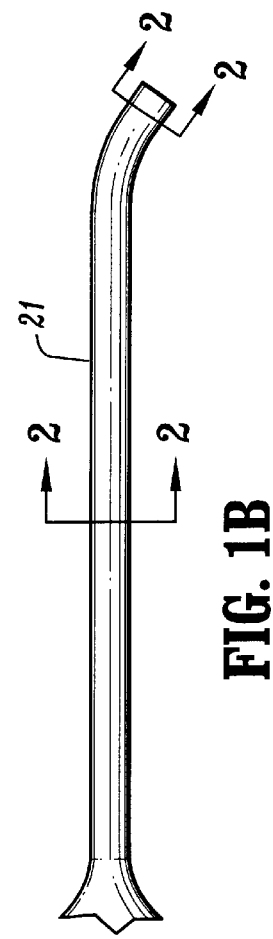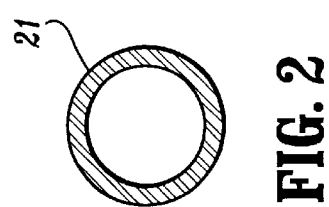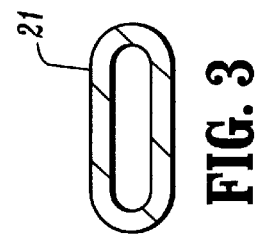

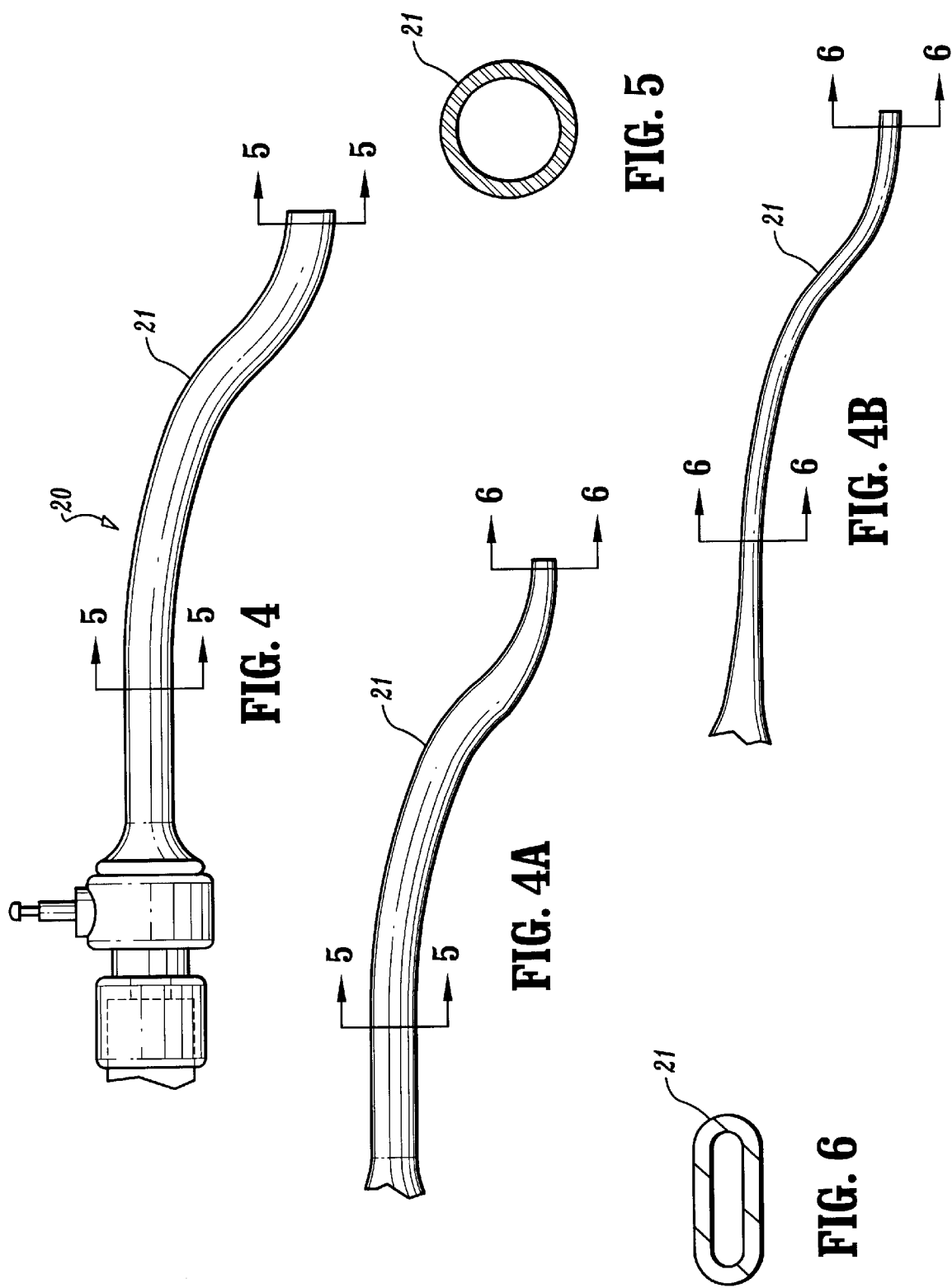

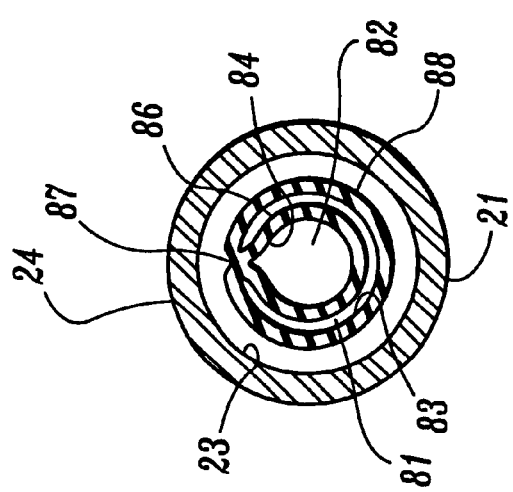
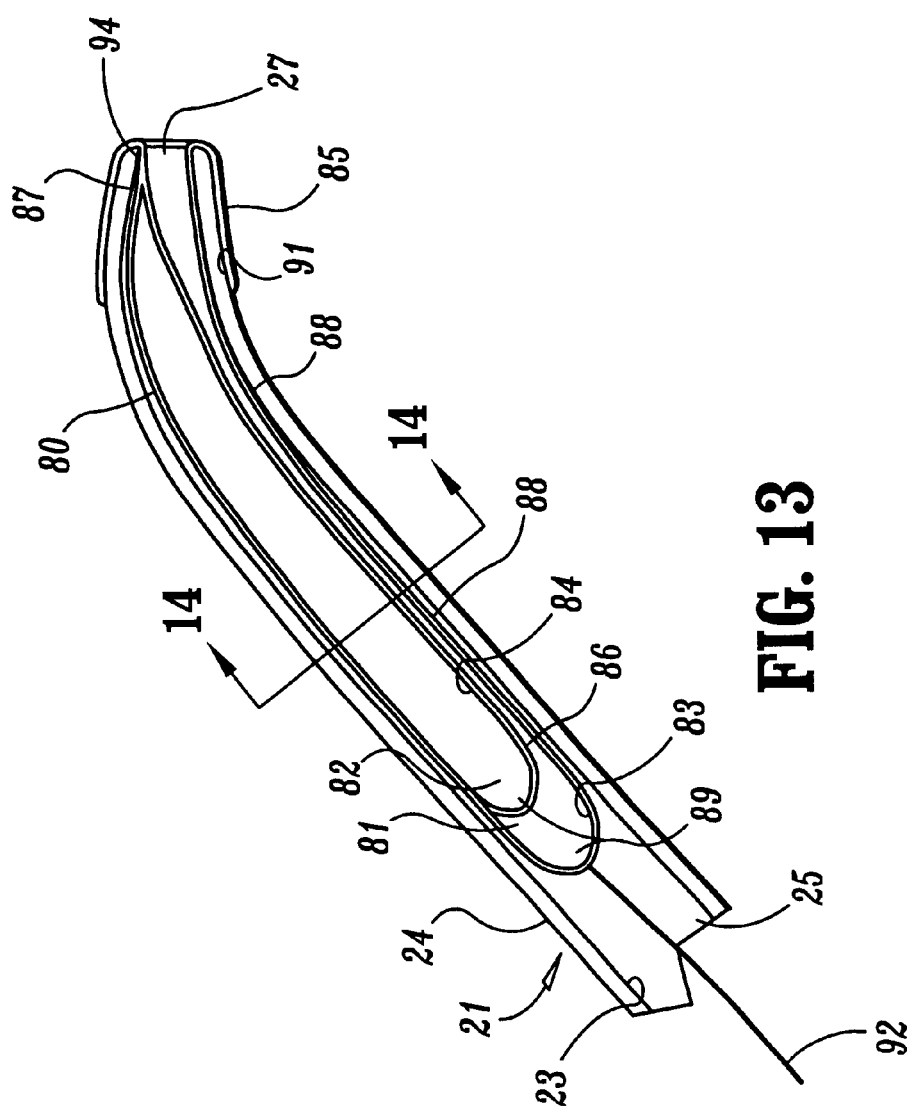

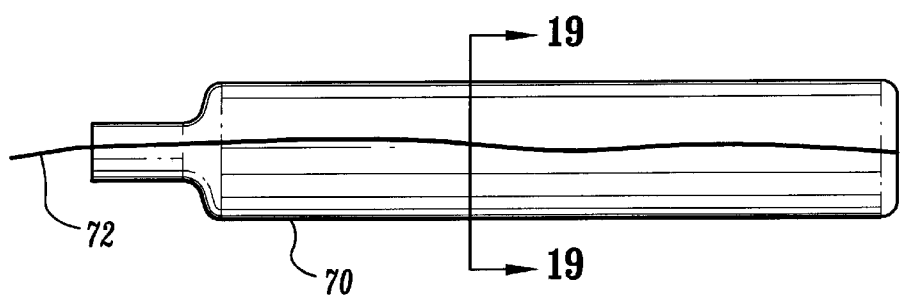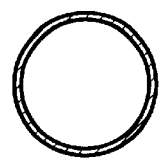
FIG. 16  FIG. 19
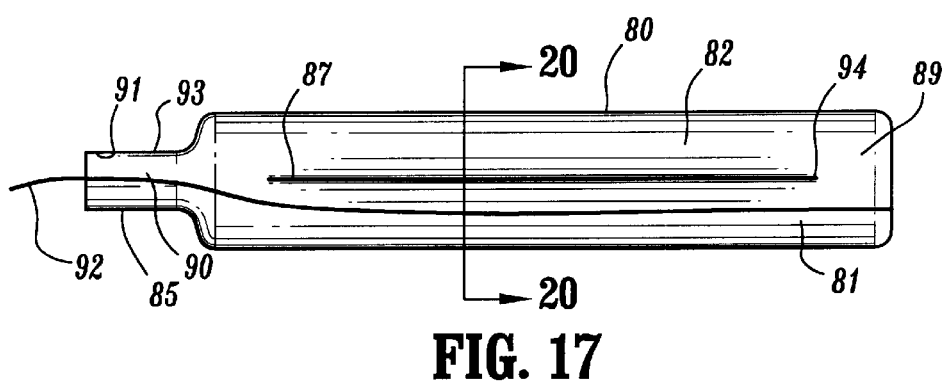
FIG. 17  FIG. 20
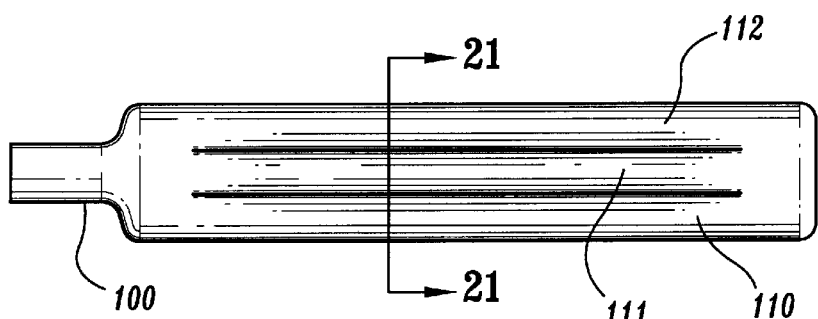
FIG. 18  FIG. 21
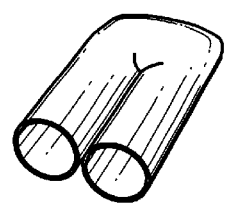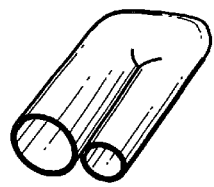
FIG. 17A  FIG. 17B

IMA DISSECTION DEVICE

FIELD OF THE INVENTION

This invention relates to harvesting blood vessels for coronary artery bypass grafting (hereinafter "CABG"), and more particularly to a device for facilitating harvesting internal mammary arteries for anastomosis to coronary arteries using minimally invasive procedures. Minimally invasive procedures are employed to minimize trauma to the patient in order to promote rapid healing and reduce the amount of pain during recovery. This invention relates particularly to a blood vessel harvesting apparatus that can be used for forming a small anatomic working space alongside an elongate vessel, particularly a blood vessel, and more particularly a small blood vessel such as an internal mammary artery (hereinafter "IMA"). The invention relates specifically to an assembly having a cannula and an assembled balloon.

BACKGROUND OF THE INVENTION

Diseases of the cardiovascular system affect millions of people each year and are a leading cause of death in the United States and throughout the world. The cost to society from such diseases is enormous both in terms of lives lost and the cost of treating cardiac disease patients through surgery. A particularly prevalent form of cardiovascular disease is a reduction in the blood supply to the heart caused by atherosclerosis or other conditions that create a restriction in blood flow in the arteries supplying blood to the heart.

Numerous surgical procedures have been developed to restore blood flow to the heart. For example, blockages can be treated with atherectomy or angioplasty, often followed by stent placement. But, when these methods of treatment cannot be used or have failed to clear the blocked artery, coronary bypass surgery may be indicated.

In the CABG procedure, the surgeon removes a portion of an artery or vein from another part of the body to use as a graft and installs the graft to bypass the obstruction. Alternatively, the surgeon dissects a healthy artery adjacent to the diseased artery, detaches one end of the healthy artery and connects that end to the coronary artery past the obstruction while leaving the other end attached to the natural arterial supply. Either of these two methods can restore normal blood flow to the heart.

The CABG procedure thus requires that one or more connections be established that bypass blockage in a diseased artery to restore an adequate blood flow. Typically, one end of a graft is sewn to the aorta, while the other end of the graft is sewn to a coronary artery, such as the left anterior descending artery (LAD), which provides blood flow to the left side of the heart. This procedure is known as a "free bypass graft." Alternatively, the IMA pedicle may be dissected free of the chest wall, while still attached to its natural arterial supply, and its distal end attached to the blocked artery distal of the obstruction. This procedure is known as an "in situ bypass graft."

In an in situ bypass graft, the IMA must be dissected free until there is sufficient length and slack in the IMA to ensure that the graft is not under tension and that it does not kink after it is repositioned. The IMAs, left and right, extend from the subclavian arteries in the neck to the diaphragm and run along the backside of the rib cage adjacent the sternum. They also contain side branches that require ligation to ensure that blood flow through the graft supplies the coronary artery, rather than being shunted off to other regions via various open branches.

Traditional methods for harvesting elongate vessels such as the IMAs involve the use of blunt probes that are pushed through body tissue to accomplish the dissection. (See Chin, U.S. Pat. No. 5,797,946, incorporated herein by reference). But, the force exerted during use of mechanical probes may lead to blood vessel trauma and branch avulsion.

Everting balloons, on the other hand, are more gentle and may be used to dissect along a vessel. But, it is difficult for the everting balloons presently available to follow vessels such as the IMAs. This is caused by the greater fixation that exists between these vessels and the tissue that surrounds them and to the characteristics of existing everting balloon dissectors. For example, a traditional everting balloon placed adjacent the saphenous vein in the leg, may squirt off in either direction upon inflation rather than track along the vein. This is due to the anatomical structures and to the fixation between the saphenous vein and the tissues that surround the vein.

Another problem associated with balloon dissectors adjacent a blood vessel is that after an initial dissection, a second dissection is more difficult. After connective tissue separating two layers of tissue has been ruptured due to an initial dissection, the healing process that ensues may involve formation of scar tissue. The scar tissue replacing the normal connective tissue is more difficult to dissect. The everting balloons presently available have difficulty tracking along a blood vessel through such scar tissue.

A need exists for new devices with adequate directional control to dissect small elongated cavities in tissue planes, particularly along the course of blood vessels, and more particularly, along the course of smaller blood vessels such as IMAs. A need also exists for new devices to dissect elongated cavities in tissue planes that have been dissected previously.

SUMMARY OF THE INVENTION

The present invention provides a cannula assembly for dissecting an elongated cavity in tissue planes, particularly along the course of a vessel, and more particularly along the course of a smaller blood vessel such as an IMA. The assembly includes an elongate tubular member comprising a hollow tube having a wall, proximal and distal ends and a lumen extending therethrough. In one embodiment, the hollow tube has a flattened or oval shaped distal end that is bent to facilitate insertion in between the ribs. Alternatively, the hollow tube can have an ogee offset at its distal end.

The dissection device also has means for connecting the hollow tube to an inflation source in order to inflate an elongate tubular balloon in fluid communication with the hollow tube. The means for connecting the hollow tube to an inflation source include an opening in the proximal end of the hollow tube or an opening in the wall of the hollow tube. Fluid, gas, or a liquid such as water or saline, can therefore be delivered from a syringe, a hand bulb pump, a piston pump, or the like to the interior of the elongate tubular balloon.

An elongate tubular balloon having an open proximal end and a closed distal end is coupled to the hollow tube and may be inverted and stored inside the hollow tube. The open proximal end of the elongate tubular balloon is coupled in a fluid-tight manner to the hollow tube. In one embodiment, the proximal end of the elongate tubular balloon is sealed around the outer wall of the hollow tube at its distal end. However, the open proximal end of the elongate tubular balloon may also be sealed to the lumen of the hollow tube or around the outer wall of the hollow tube at its proximal end.

The distal portion of the deflated elongate tubular balloon can be inverted toward the proximal portion and stored inside the hollow tube or in a reservoir formed in the balloon itself. Thus, in its deflated state, the distal end of the elongate tubular balloon may be stored proximal of its proximal end. Additional inward folds may be used to further shorten the length of the deflated elongate tubular balloon.

During inflation, this inverted embodiment of the elongate tubular balloon everts and advances beyond the distal end of the hollow tube until it is completely inflated. The fully inflated elongate tubular balloon can be as long as or longer than the hollow tube.

The dissection device also comprises a means for deflating the elongate tubular balloon, such as a vent or a deflation valve on the hollow tube. The elongate tubular balloon may be inflated and deflated multiple times during a single use.

The dissection device may also include means for retracting and re-inverting the elongate tubular balloon so that it can be re-inflated for multiple use during a surgical procedure. Means for retracting and re-inverting may include push rods, guide rods, or retraction lines comprising wire or string attached to the distal portion of the balloon.

It can be appreciated that the elongate tubular balloon of the present invention can have multiple chambers running substantially the entire length of the balloon. Multiple chambers serve to add lateral rigidity to the elongate balloon as it inflates while minimizing the cross-section of the dissected space created. The elongate tubular balloon can have one chamber, more preferably five chambers, more preferably four chambers, more preferably three chambers and most preferably two chambers. However, other embodiments having a greater number of chambers are also contemplated.

It has been found preferable to utilize a nonelastomeric balloon so that it is possible to control the shape of the dissected region. The fully inflated balloon can have an axial length of 5 to 30 inches, a width of 0.50 to 2.5 inches, and a height of 0.10 to 1.0 inches. The balloon can be formed as described in Kieturakis et al., U.S. Pat. No. 5,496,345, the entirety of which is incorporated herein by reference.

In one embodiment, the elongate tubular balloon has two cylindrical chambers running substantially the entire length of the balloon. The two chambers are in fluid communication with each other. A weld running substantially the entire length of the balloon may accomplish this double chambered configuration. The double chambered configuration decreases the likelihood that the everting balloon will track laterally off course as it everts, and it also eases insertion and tracking along the narrow space available between the sternum and the IMA and other surrounding tissue.

The double chambered configuration flattens the elongate tubular balloon, thus making it easier for the elongate tubular balloon to settle into a natural tissue plane. With a wider profile and a decreased height, the elongate tubular balloon is more likely to track along a natural tissue plane without changing its course laterally in an undesirable direction. If desired, the elongate tubular balloon may be curved to follow a desired path.

Moreover, with a left chamber and a right chamber, the lateral rigidity of the elongate tubular balloon increases for any given cross-section. This is because the width of an elongate tubular balloon that has been flattened by adding a weld along its length is greater than the height of the balloon. Thus, the moment of inertia will be higher in the plane defined by the width of the elongate tubular balloon than in the plane defined by the height of the elongate tubular balloon. Therefore, the double chambered configuration of the present invention will be less likely to bend transversely toward the left or right chambers as it everts along a natural tissue plane. Furthermore, it is not likely to bend in an upward or downward direction since it will be prevented from doing so by both the natural tissue layer above it and the natural tissue layer below it. Therefore, the double chambered everting elongate tubular balloon of the present invention is better suited for controlled dissection along smaller arteries such as the IMAs, which are tightly adhered to the tissue that surrounds them.

The flattened profile of the double chambered balloon is also desirable because the distance from the sternum to either the right or left IMA is about half an inch. This distance does not change substantially at any point along the length of either of the IMAs. Therefore, a flatter profile balloon is preferred to track along the narrow space available between the sternum and the IMA. Furthermore, a flat profile balloon is preferred over a thin and round balloon for dissecting along arteries such as IMAs for the reasons stated above with respect to lateral rigidity.

In a cannula assembly comprising a double chambered elongate tubular balloon, the balloon can be inverted by pulling or pushing the distal end of the balloon proximally through one of the chambers. Thus, in a deflated state, one of the chambers of the double chambered elongate tubular balloon is stored inside the other inverted chamber. Substantially the entire length of the deflated elongate tubular balloon can be stored inside the hollow tube. Upon inflation, the distal end of the balloon begins to evert outwardly and propagate in a distal direction until the balloon has completely everted and extends outside of the hollow tube. The propagation of the everting balloon can be facilitated by coating the internal surface, the external surface, or both surfaces of the balloon with a lubricant.

Alternatively, the two cylindrical chambers of the elongate tubular balloon can be formed by shifting the line of the weld to one side, thus resulting in one chamber having a larger cross-section than the other. This configuration may ease inversion and eversion, because there is a larger inverting chamber into which the smaller chamber follows during inversion and from which it exits during eversion.

In other embodiments of the present invention, the elongate tubular balloon has three, four or five chambers running substantially the entire length of the balloon. The chambers can be in fluid communication with each other or entirely separated and separately inflated. Welds running substantially the entire length of the balloon accomplish these configurations. Like the double-chambered elongate tubular balloon, the three, four and five-chambered configurations decrease the likelihood that the everting balloons will track off course as they evert, and they also ease insertion and tracking along the narrow space available between the sternum and the IMA. However, elongate tubular balloons having more than five chambers are also contemplated.

In another embodiment the dissection device is designed for use with an endoscope or laparoscope. The proximal end of the hollow tube of the dissection device is adapted to receive, and if necessary, seal around the scope. The scope can be inserted through the proximal end of the hollow tube and advanced toward the distal end of the hollow tube either while the elongate tubular balloon is being inflated or after the elongate tubular balloon is completely inflated and is in its everted position. In the case of a multi-chambered elongate tubular balloon, the scope can be, advanced through any one of the chambers. Alternatively, the scope can be independently inserted through the incision and advanced alongside the elongate tubular balloon as the balloon everts and dissects along the IMA or after the balloon is fully inflated.

Another embodiment of the dissection device comprises a guide rod, the distal end of which is inserted through the proximal end of the hollow tube and attached to the distal end of the elongate tubular balloon. Thus, eversion of the elongate tubular balloon and dissection along the IMA can be done either by advancing the guide rod along the IMA while inflating the balloon at the same time, or by advancing the guide rod along the IMA to the desired point and thereafter inflating the elongate tubular balloon. The guide rod can also be used to retract the elongate tubular balloon back into the hollow tube, at the same time re-inverting the elongate tubular balloon for withdrawal or subsequent use. A guide rod can be used either in a single chambered elongate tubular balloon or a multi-chambered elongate tubular balloon and may be attached to the distal end of the balloon, or may be loose.

Another embodiment of the dissection device comprises a guide rod, as above described, which is attached to a shorter balloon having a larger cross-section upon inflation. The hollow tube of this embodiment is longer than in the other embodiments earlier described to compensate for the decreased length of the balloon. Dissection is accomplished by 1) advancing the guide rod a short distance along, for example the IMA, for blunt dissection, probing between the IMA and the adjacent tissue in the plane initiated by this method of blunt dissection, 2) inflating the balloon to further dissect the IMA from the tissue adjacent to it, 3) deflating the balloon and 4) repeating steps one through three along the length of the IMA desired for the coronary artery bypass graft.

Another embodiment of the invention comprises a double-chambered elongate tubular balloon having a laterally extending thumb-shaped reservoir. A housing having a tubular balloon sleeve extending therefrom terminates the balloon and may receive a laparoscope. In its deflated and undeployed state, one chamber of the balloon is stored within the other chamber as previously described, and the distal portion of the balloon is stored inside the thumb-shaped reservoir.

Additional features of the invention will appear from the following description in which the preferred embodiments are set forth in detail in conjunction with the accompanying drawings.

BRIEF DESCRIPTION OF THE DRAWINGS

Reference is next made to a brief description of the drawings, which are intended to illustrate devices for dissection adjacent elongate structures, particularly for harvesting blood vessels, particularly those useful in dissecting along IMAs. The drawings and detailed descriptions which follow are intended to be merely illustrative and are not intended to limit the scope of the invention as set forth in the appended claims.

FIG. 1 is a side elevational view of a dissection device of the present invention.

FIG. 1A is an alternate embodiment of the elongate tubular member of the dissection device of FIG. 1, wherein the elongate tubular member is flattened.

FIG. 1B is another alternate embodiment of the elongate tubular member of the dissection device of FIG. 1, wherein the distal end of the elongate tubular member has a round opening rather than a flattened opening.

FIG. 2 is a cross-sectional view taken along lines 2—2 in FIGS. 1 and 1B.

FIG. 3 is a cross-sectional view taken along lines 3—3 in FIGS. 1 and 1A.

FIG. 4 is a side elevational view of a dissection device of the present invention, said dissection device having an Ogee curve.

FIG. 4A is an alternate embodiment of the elongate tubular member of the dissection device of FIG. 4, wherein the distal end of the elongate tubular member has a flattened opening rather than a round opening.

FIG. 4B is another alternate embodiment of the elongate tubular member of the dissection device of FIG. 4, wherein the elongate tubular member is flattened.

FIG. 5 is a cross-sectional view taken along lines 5—5 in FIGS. 4 and 4A.

FIG. 6 is a cross-sectional view taken along lines 6—6 in FIGS. 4A and 4B.

FIGS. 13 is a side elevational view of a hollow tube with an inverted double-chambered elongate tubular balloon.

FIG. 14 is a cross-sectional view taken along line 14—14 in FIG. 13.

FIG. 16 is a plan view of an everted elongate tubular balloon.

FIG. 17 is a plan view of an everted double-chambered elongate tubular balloon.

FIG. 17A is a three-dimensional view of the double-chambered elongate tubular balloon of FIG. 17.

FIG. 17B is a three-dimensional view of an alternate embodiment of the double-chambered elongate tubular balloon of FIG. 17, wherein one of the chambers has a smaller cross-sectional area than the other chamber.

FIG. 18 is a plan view of an everted three-chambered elongate tubular balloon.

FIG. 19 is a cross-sectional view taken along line 19—19 in FIG. 16.

FIG. 20 is a cross-sectional view taken along line 20—20 in FIG. 17.

FIG. 21 is a cross-sectional view taken along line 21—21 in FIG. 18.

DETAILED DESCRIPTION OF THE PREFERRED EMBODIMENT

Figure 7:
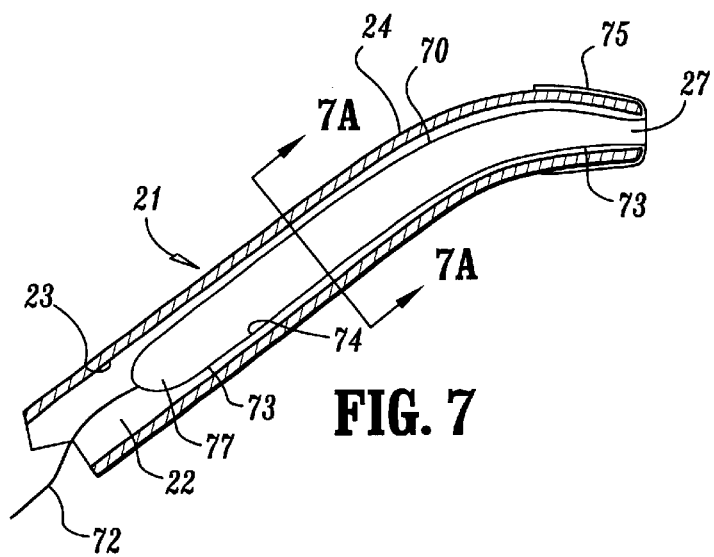
FIG. 7 is a side elevational view of a hollow tube with an inverted elongate tubular balloon.

In the embodiment illustrated in FIG. 1, an IMA dissection device 10 includes an elongate tubular member 20, a deflation valve 30, a hand pump 40, an inflation port 50, and a handle 60. The elongate tubular member 20 comprises a hollow tube 21 having an opening 25 in its proximal end, the opening 25 being in fluid communication with the inflation port 50 and the deflation valve 30. The distal end of the hollow tube 21 is bent to facilitate insertion in between the ribs and has an opening 27, which can either be flattened, as shown in FIGS. 1, 1A and 3, or circular as shown in FIGS. 1B and 2. Furthermore, the entire length of the hollow tube 21 can be flattened as shown in FIG. 1A or can have a circular cross-section, as shown in FIG. 1B.

Hand pump 40 is a means for inflating balloons that are stored in the hollow tube 21, as shown in later figures. However, other means of inflation include a syringe in fluid communication with an inflation lumen, such as the inflation lumen 66, shown in FIG. 10.

The hollow tube 21 can have an ogee offset at its distal end as shown in FIGS. 4, 4A and 4B. The distal end of the hollow tube 21 can either have a circular opening, as shown in FIGS. 4 and 5, or a flattened opening, as shown in FIGS. 4A, 4B and 6. Furthermore, the entire length of the hollow tube 21 can be flattened as shown in FIG. 4B or can have a circular cross-section, as shown in FIG. 4.

Figure 8:
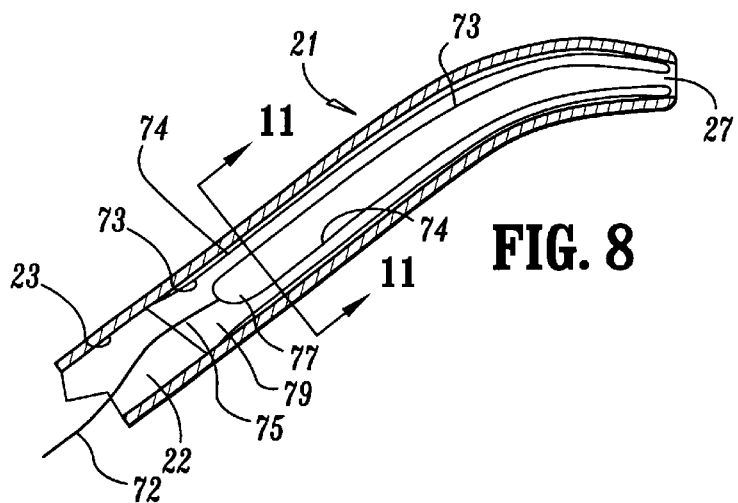
FIG. 8 is an alternate embodiment of the device depicted in FIG. 7, wherein the elongate tubular balloon is sealed to the luminal surface of the hollow tube.
Figure 9:
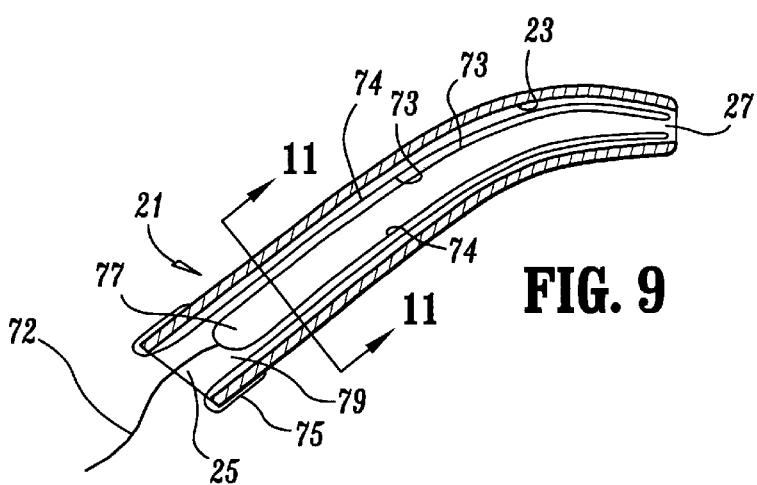
FIG. 9 is another alternate embodiment of the device depicted in FIG. 7, wherein the elongate tubular balloon is wrapped over the proximal end of the hollow tube and sealed to the outer wall at the proximal end of the hollow tube.

As shown in FIGS. 7, 8 and 9, an elongate tubular balloon 70 is coupled to the hollow tube 21. The elongate tubular balloon 70 has a proximal end 75 with an opening and a distal end 77 with no opening and an optional retraction line 72 attached to the luminal surface 73 of the inverted portion of the elongate tubular balloon 70 at its distal end 77. The open proximal end 75 of the elongate tubular balloon 70 is coupled in a fluid-tight manner to the hollow tube 21 by sealing the entire circumference of the luminal surface 73 of the proximal uninverted end 75 of the elongate tubular balloon 70 around the outer wall 24 of the hollow tube 21 at its distal end. This is accomplished by pulling the opening of the proximal end 75 of the elongate tubular balloon 70 over the distal end and distal opening 27 of the hollow tube 21, and using, for example, an adhesive material, a sealing ring or collar, or just a tight fit to seal the luminal surface 73 of the proximal uninverted end 75 of the elongate tubular balloon 70 to the outer wall 24 of the hollow tube 21 at its distal end.

The elongate tubular balloon 70 may be sealed to the hollow tube 21 in other configurations as well. For example, the outer wall 74 at the proximal end 75 of the elongate tubular balloon 70 may be sealed to the luminal surface 23 of the hollow tube 21, as shown in FIG. 8. In another example, the outer wall 74 at the proximal end 75 of the elongate tubular balloon 70 may be wrapped over the proximal opening 25 of the hollow tube 21 and sealed to the outer wall 24 at the proximal end of the hollow tube 21, as shown in FIG. 9.

Figure 10:
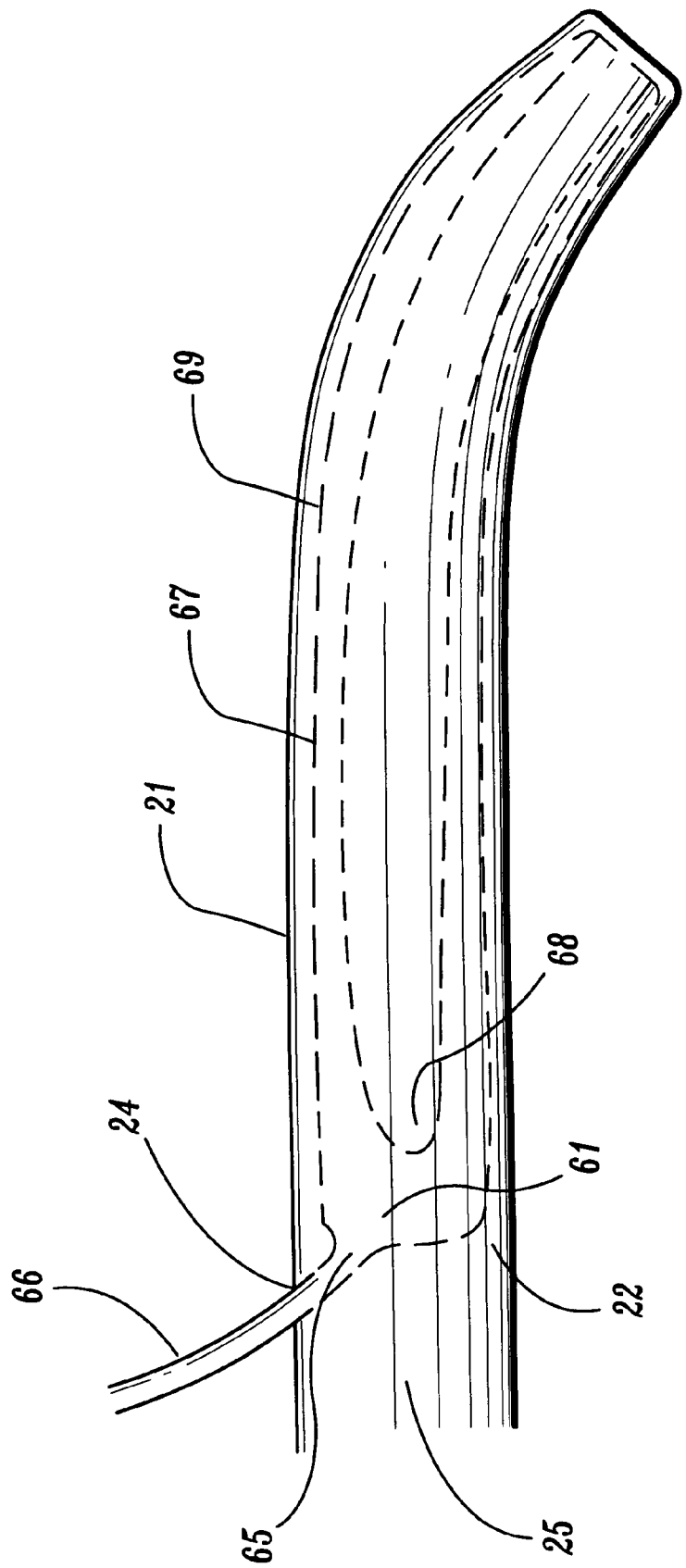
FIG. 10 is a side elevational view of another alternate embodiment of the device depicted in FIG. 7, wherein the elongate tubular balloon has an inflation lumen.

Alternatively, it is contemplated that an elongate tubular balloon 69, as shown in FIG. 10, has no openings, other than an opening 65 for connection to an inflation lumen 66. The elongate tubular balloon 69 is inverted and stored inside the hollow tube 21, but need not be sealed to the hollow tube 21. Moreover, the opening 65 may be on the lateral wall 67 of the elongate tubular balloon 69 and not on the proximal end 61 of the elongate tubular balloon 69. Thus, both the proximal end 61 of the elongate tubular balloon 69 and the distal end 68 of the elongate tubular balloon 69 may be closed. The inflation lumen 66 may be introduced into the luminal space 22 of the hollow tube 21 through either the proximal opening 25 of the hollow tube 21 or a lateral opening 24 on the hollow tube 21, as shown in FIG. 10.

Figure 7A:
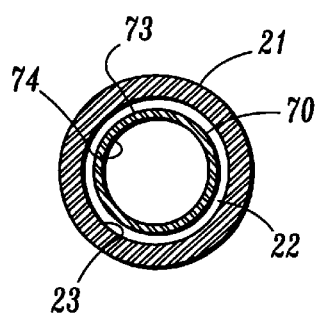
FIG. 7A is a cross-sectional view taken along lines 7A—7A in FIG. 7.

In the embodiments shown in FIGS. 7, 7A, 8, 9, and 11 the elongate tubular balloon 70 is in a deflated state and is inverted and stored in the luminal space 22 of the hollow tube 21. FIG. 7A is a cross-section taken through line 7A—7A of FIG. 7. For the sake of visual clarity, FIG. 7A does not show contact between the luminal surface 73 of the inverted portion of the elongate tubular balloon 70 and the luminal surface 23 of the hollow tube 21. However, it can be appreciated that the inverted balloon 70 may be in contact with the luminal surface 23 of the hollow tube 21 at various cross-sectional areas along the length of the elongate tubular balloon 70.

Figure 11:
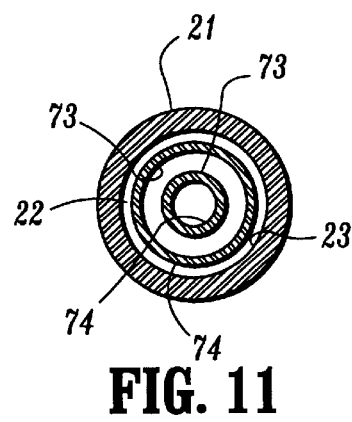
FIG. 11 is a cross-sectional view taken along lines 11—11 in FIGS. 8 and 9.

FIG. 11 is a cross-section taken through 11—11 of FIGS. 8 and 9. Again for the sake of visual clarity, FIG. 11 does not show contact between the luminal surface 73 of the uninverted portion of the elongate tubular balloon 70 and the luminal surface 73 of the inverted portion of the elongate tubular balloon 70. Likewise, there is no contact shown between the luminal surface 23 of the hollow tube 21 and the outer wall 74 of the elongate tubular balloon 70. However, it can be appreciated that the luminal surface 73 of the uninverted portion of the elongate tubular balloon 70 and the luminal surface 73 of the inverted portion of the elongate tubular balloon 70 may be in contact at various cross-sectional areas along the length of the elongate tubular balloon 70. Likewise, the luminal surface 23 of the hollow tube 21 and the outer wall 74 of the elongate tubular balloon 70 may also be in contact at various cross-sectional areas along the length of the elongate tubular balloon 70.

Figure 12:
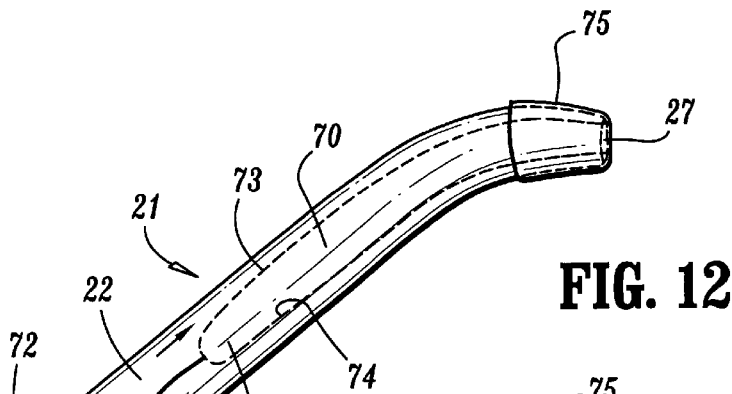
FIG. 12 is a side elevational view of a hollow tube with an inverted elongate tubular balloon as fluid is introduced into the hollow tube.
Figure 12A:
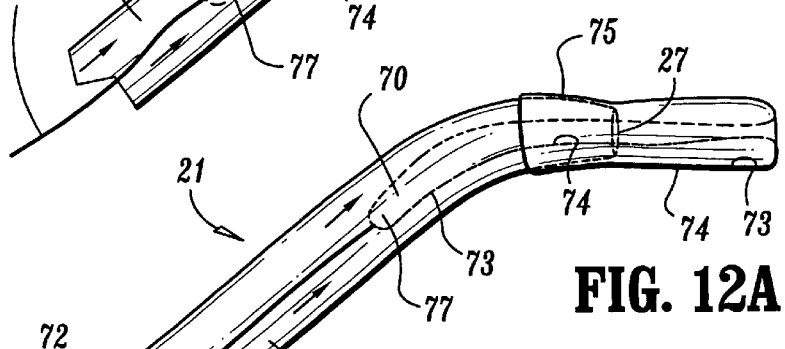
FIGS. 12A, 12B and 12C are side elevational views of the elongate tubular balloon of FIG. 12 as it everts due to introduction of fluid.
Figure 12B:
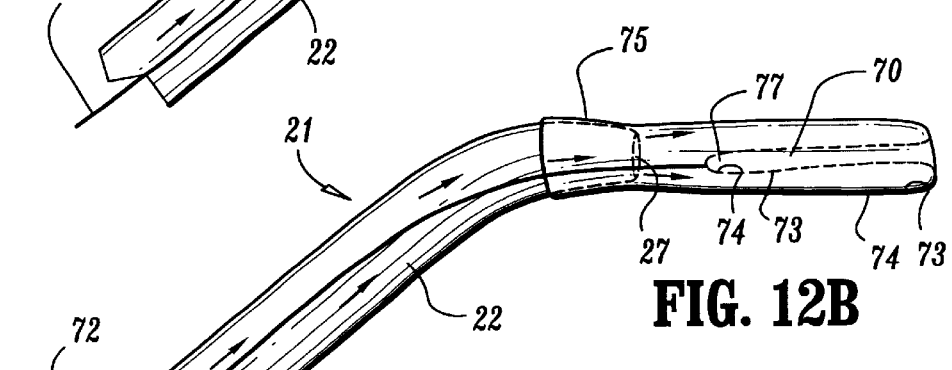
Figure 12C:
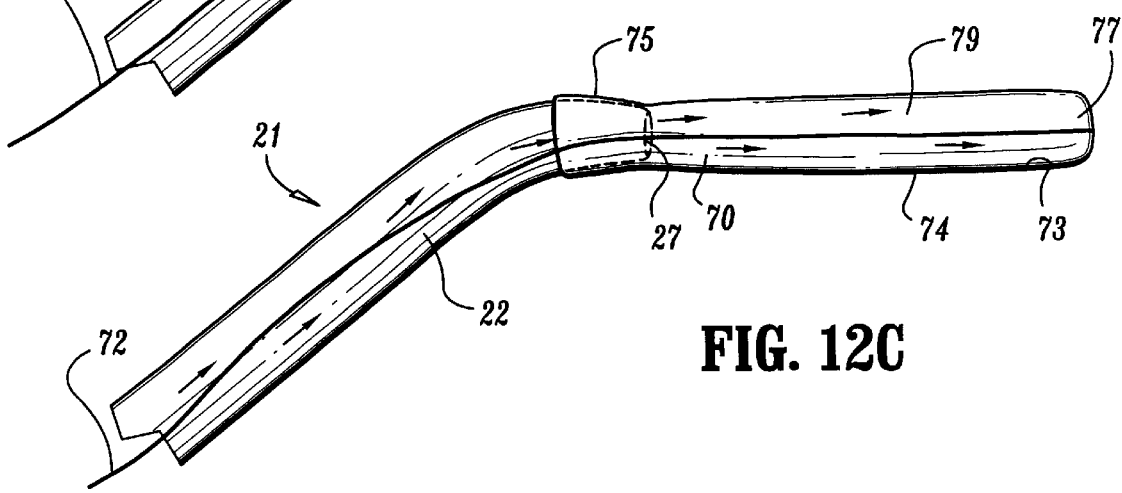

Inflation of the elongate tubular balloon 70 is shown in FIGS. 12, 12A, 12B and 12C. In the initial deflated and inverted state, distal end 77 of the elongate tubular balloon 70 is proximal of the proximal end 75 of the elongate tubular balloon 70. However, as fluid is introduced into the luminal space 22 of the hollow tube 21 and inflation progresses, the proximal end 75 of the elongate tubular balloon 70 begins to inflate distally, pulling the distal end 77 in a distal direction toward the opening 27 of the hollow tube. Fluid forces the inverted elongate tubular balloon 70 to evert until the elongate tubular balloon 70 is fully inflated and entirely outside the luminal space 22 of the hollow tube 21, as shown in FIG. 12C. It can also be appreciated that in the case of either of the embodiments shown in FIGS. 8 and 9, fluid can be delivered directly to the luminal space 79 of the uninverted portion of the elongate tubular balloon 70. Furthermore, in the embodiments shown in FIGS. 8 and 9 only the inverted portion of the elongate tubular balloon 70 will propagate distally and will advance outside the luminal space 22 of the hollow tube 21 upon inflation. The retraction line 72 can be used to retract and re-invert the elongate tubular balloon 70 back into the hollow tube 21 for multiple use during a procedure.

In another embodiment as shown in FIG. 13, the elongate tubular balloon 80 comprises two cylindrical chambers: an outer chamber 81 and an inner chamber 82. As shown in FIG. 17, the two chambers 81 and 82 are in fluid communication with each other, but are separated for substantially the entire length of the elongate tubular balloon 80 by a weld 87. The proximal end 85 of the double chambered elongate tubular balloon 80 comprises a single chamber 90. The single chamber 90 splits into two chambers 81 and 82 at the point where the weld 87 begins. At the point where the weld 87 ends, which is at the distal end 89 of the double chambered elongate tubular balloon 80, the two chambers 81 and 82 may converge into one.

Although FIG. 13 shows the two chambers 81 and 82 converging at the point 94 where the weld 87 ends, it is contemplated that the weld 87 may run to the very distal end 89 of the double-chambered elongate tubular balloon 80. In an embodiment in which the weld 87 runs to the very distal end 89 of the elongate tubular balloon 80, the two chambers 81 and 82 remain separated at the distal end 89.

The two chambers 81 and 82 may be symmetrical as shown in FIG. 17A, or the outer chamber 81 may have a larger cross-section than the inner chamber 82 as shown in FIG. 17B. In the deflated and inverted state, the two chambers 81 and 82 are stored in the luminal space 22 of the hollow tube 21. Furthermore, chamber 82 is stored in the inverted outer chamber 81.

FIG. 14 is a cross-sectional view of FIG. 13, showing the inner chamber 82 stored in the inverted outer chamber 81. FIG. 14 also shows the weld 87 separating the two chambers 81 and 82. For the sake of visual clarity, FIG. 14 does not show the inverted outer wall 83 of the outer chamber 81 in contact with the outer wall 86 of the inner chamber 82 at any point other than the weld 87. Nor does FIG. 14 show contact between the inverted luminal surface 88 of the outer chamber 81 and the luminal surface 23 of the hollow tube 21. However, it can be appreciated that there may be contact between the inverted outer wall 83 of the outer chamber 81 and the outer wall 86 of the inner chamber 82 at various cross-sectional areas along the length of the double chambered elongate tubular balloon 80. Likewise, there may be contact between the inverted luminal surface 88 of the outer chamber 81 and the luminal surface 23 of the hollow tube 21 at various cross-sectional areas along the length of the double chambered elongate tubular balloon 80.

In another embodiment as shown in FIG. 17B, the cross-sectional area of the outer chamber 81 is larger than the cross-sectional area of the inner chamber 82. This asymmetrical configuration eases inversion because the greater diameter of the outer chamber 81 serves to decrease the amount of contact and friction between the inverted outer wall 83 of the outer chamber 81 and the outer wall 86 of the inner chamber 82. Likewise, the asymmetrical configuration also eases eversion, because there is more space hence less friction between the inverted outer wall 83 of the outer chamber 81 and the outer wall 86 of the inner chamber 82 during eversion. Also, the double-chambered elongate tubular balloon 80 may be lubricated to decrease the amount of friction and ease inversion and eversion. For example, luminal surfaces 84 and 88 of the respective chambers 82 and 81 and/or the outer walls 86 and 83 of the respective chambers 82 and 81 may be lubricated. The lubricant used can be clear if an endoscope or laparoscope is to be inserted into the balloon for visualization of dissected tissue layers.

Figure 15:
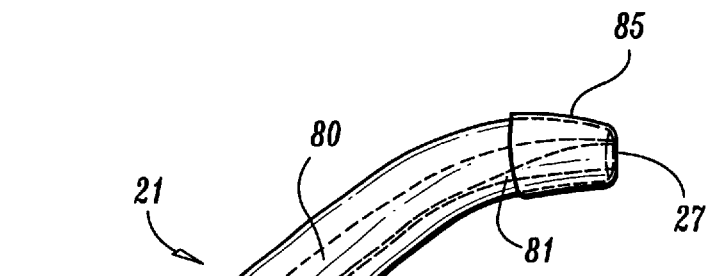
FIG. 15 is a side elevational view of a hollow tube with an inverted double-chambered elongate tubular balloon as fluid is introduced into the hollow tube.
Figure 15A:
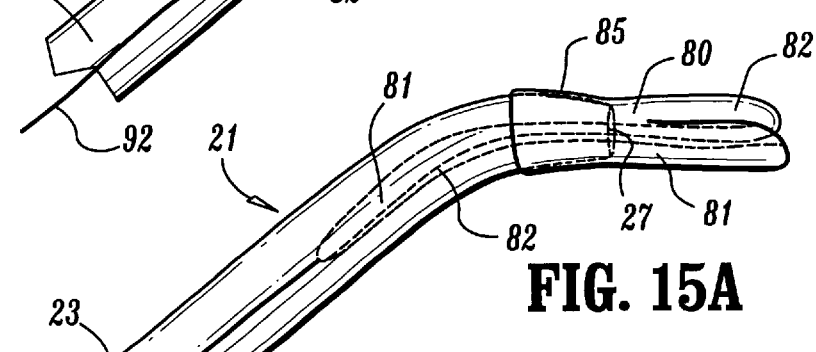
FIGS. 15A, 15B and 15C are side elevational views of the double-chambered elongate tubular balloon of FIG. 15 as it everts due to introduction of fluid.
Figure 15B:
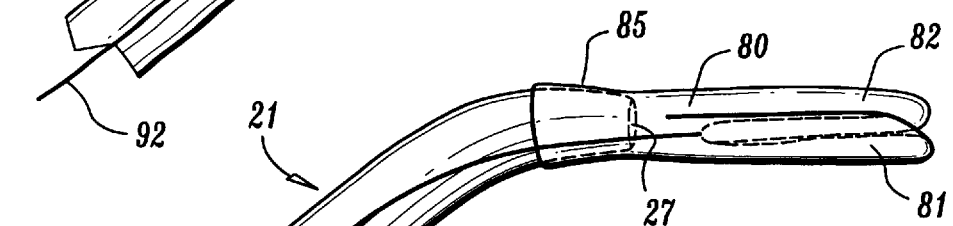
Figure 15C:
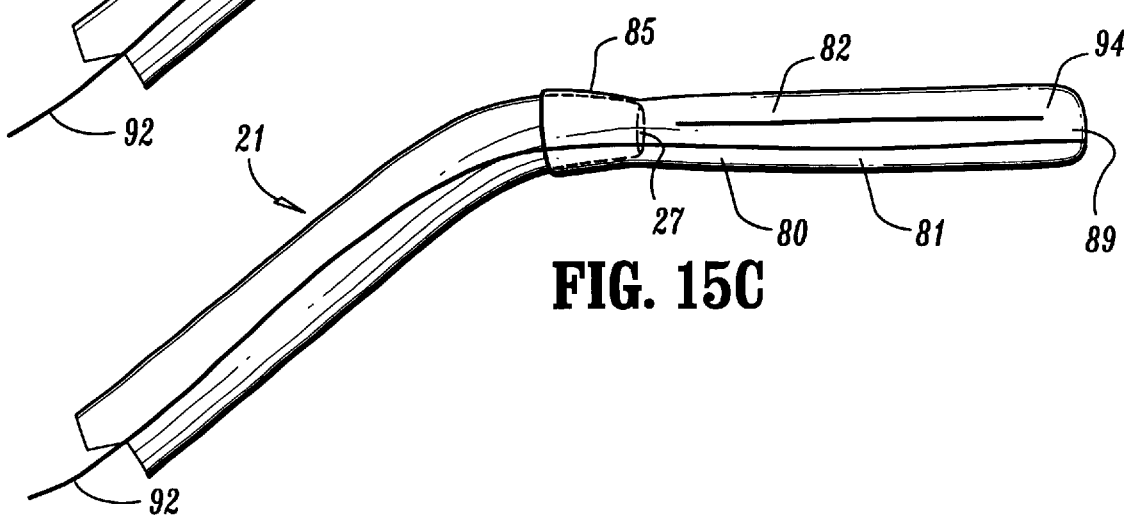

Inflation of the double chambered elongate tubular balloon 80 is shown in FIGS. 15, 15A, 15B and 15C. In the initial deflated and inverted state, distal end 89 of the double chambered elongate tubular balloon 80 is proximal of the proximal end 85 of the double chambered elongate tubular balloon 80. However, as fluid is introduced into the luminal space 22 of the hollow tube 21 and inflation progresses, the double chambered elongate tubular balloon 80 begins to inflate and evert distally from its proximal end 85, pulling the distal end 89 in a distal direction toward the opening 27 of the hollow tube. Fluid forces the inverted outer chamber 81 of the double chambered elongate tubular balloon 80 to evert, while the inner chamber 82 is expelled, progressively rotating out of the outer chamber 81. FIG. 15C shows the double chambered elongate tubular balloon 80 fully inflated and entirely outside the luminal space 22 of the hollow tube.

After the double chambered elongate tubular balloon 80 is fully inflated, it can be deflated by a variety of means including a deflation valve or a vent on the hollow tube 21. Once the elongate tubular balloon 80 is deflated it can be removed from the patient, or it can be retracted and re-inverted back into the hollow tube 21 with a retraction line 92. The retraction line 92 may be attached to the luminal surface of the elongate tubular balloon at its distal end 89 as shown in FIG. 15C. Alternatively, if the weld 94 runs to the very distal end 89 of the elongate tubular balloon 80 so that the two chambers 81 and 82 are separated at the distal end, the retraction line 92 may be attached to the luminal surface 88 of the outer chamber 81 at its distal end. The retraction line 92 can be used to re-invert the double chambered elongate tubular balloon 80 for multiple use during a procedure. The retraction line may comprise, for example, wire, string or nylon thread.

The open proximal end 85 of the elongate tubular balloon 80 is coupled in a fluid-tight manner to the hollow tube 21 by sealing the entire circumference of the luminal surface 91 of the proximal uninverted end 85 of the elongate tubular balloon 80 around the outer wall 24 of the hollow tube 21 at its distal end. This is accomplished by pulling the opening of the proximal end 85 of the elongate tubular balloon 80 over the distal end and distal opening 27 of the hollow tube 21, and using, for example, an adhesive material, a sealing ring or collar, or just a tight fit to seal the luminal surface 91 of the proximal uninverted end 85 of the elongate tubular balloon 80 to the outer wall 24 of the hollow tube 21 at its distal end.

The elongate tubular balloon 80 may be sealed to the hollow tube 21 in other configurations as well. For example, the outer wall 93 at the proximal end 85 of the elongate tubular balloon 80 may be sealed to the luminal surface 23 of the hollow tube 21, as in the single chambered elongate tubular balloon 70 shown in FIG. 8. In another example, the outer wall 93 at the proximal end 85 of the elongate tubular balloon 80 may be wrapped over the proximal opening 25 of the hollow tube 21 and sealed to the outer wall 24 at the proximal end of the hollow tube 21, as in the single chambered elongate tubular balloon 70 shown in FIG. 9.

Figure 13A:
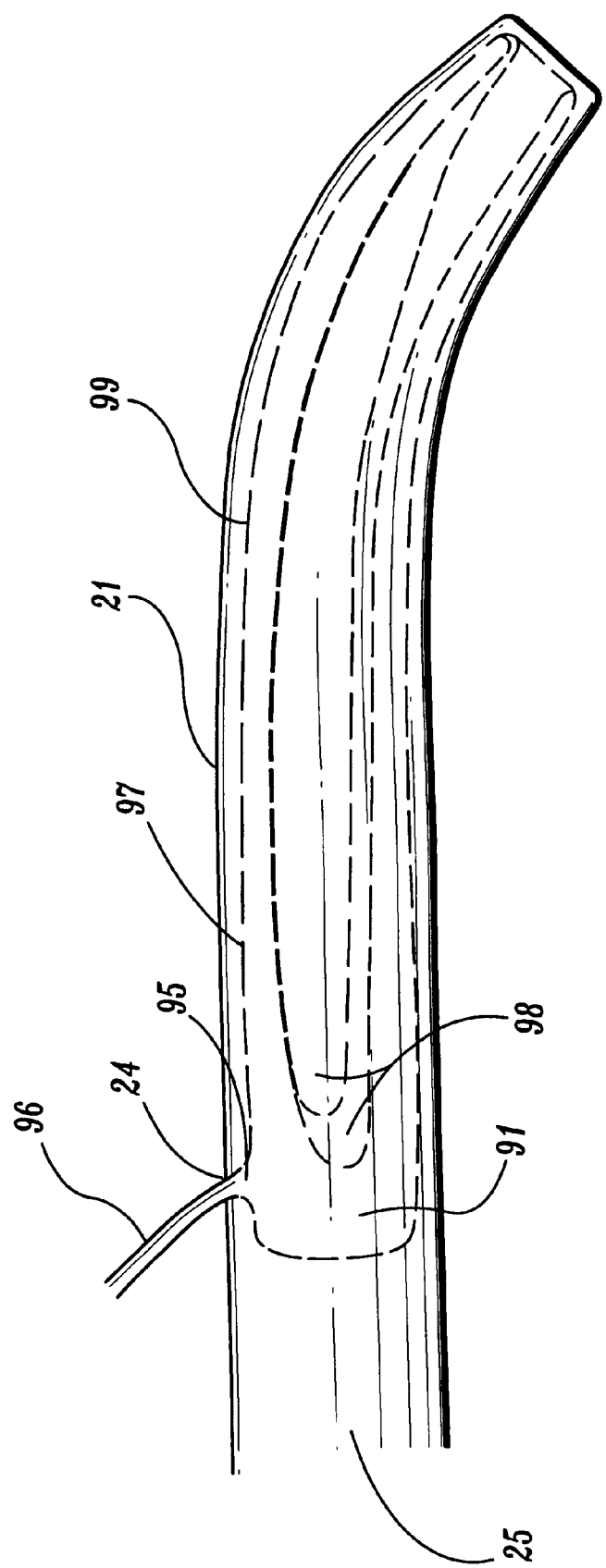
FIG. 13A is an alternative embodiment of the device depicted in FIG. 13, wherein the elongate tubular balloon has an inflation lumen.

Alternatively, it is contemplated that a double-chambered elongate tubular balloon 99, as shown in FIG. 13A, has no openings, other than an opening 95 for connection to an inflation means 96. The double-chambered elongate tubular balloon 99 is inverted, with one chamber stored inside the other as previously described. The double-chambered elongate tubular balloon 99 itself is stored inside the hollow tube 21, but need not be sealed to the hollow tube 21. Moreover, the opening 95 may be on the lateral wall 97 of the elongate tubular balloon 99, as shown in FIG. 13A, or on the proximal end 91 of the elongate tubular balloon 99. The inflation lumen 96 may be introduced into the luminal space 22 of the hollow tube 21 through either a lateral opening 24 on the hollow tube 21, as shown in FIG. 13A, or the proximal opening 25 of the hollow tube 21.

Alternatively, as shown in FIGS. 18 and 21, the elongate tubular balloon 100 can comprise three chambers, 110, 111 and 112. In an inverted three chambered configuration, two of the chambers would be stored inside the inverted outer wall of the third chamber. The three chambered configuration may have a large proximal opening such as the one shown in FIG. 18, or a small lateral or proximal opening for connection to an inflation means, such as shown in FIGS. 10 and 13A. For ease of inversion and eversion, the chamber storing the other two chambers during the deflated and inverted state can have a larger cross-section than the other two chambers. Lubricant may also be used on the outer and/or inner walls of the elongate tubular balloon to ease inversion and eversion. Furthermore, although not shown, configurations with more than three chambers are also contemplated.

Figure 22:
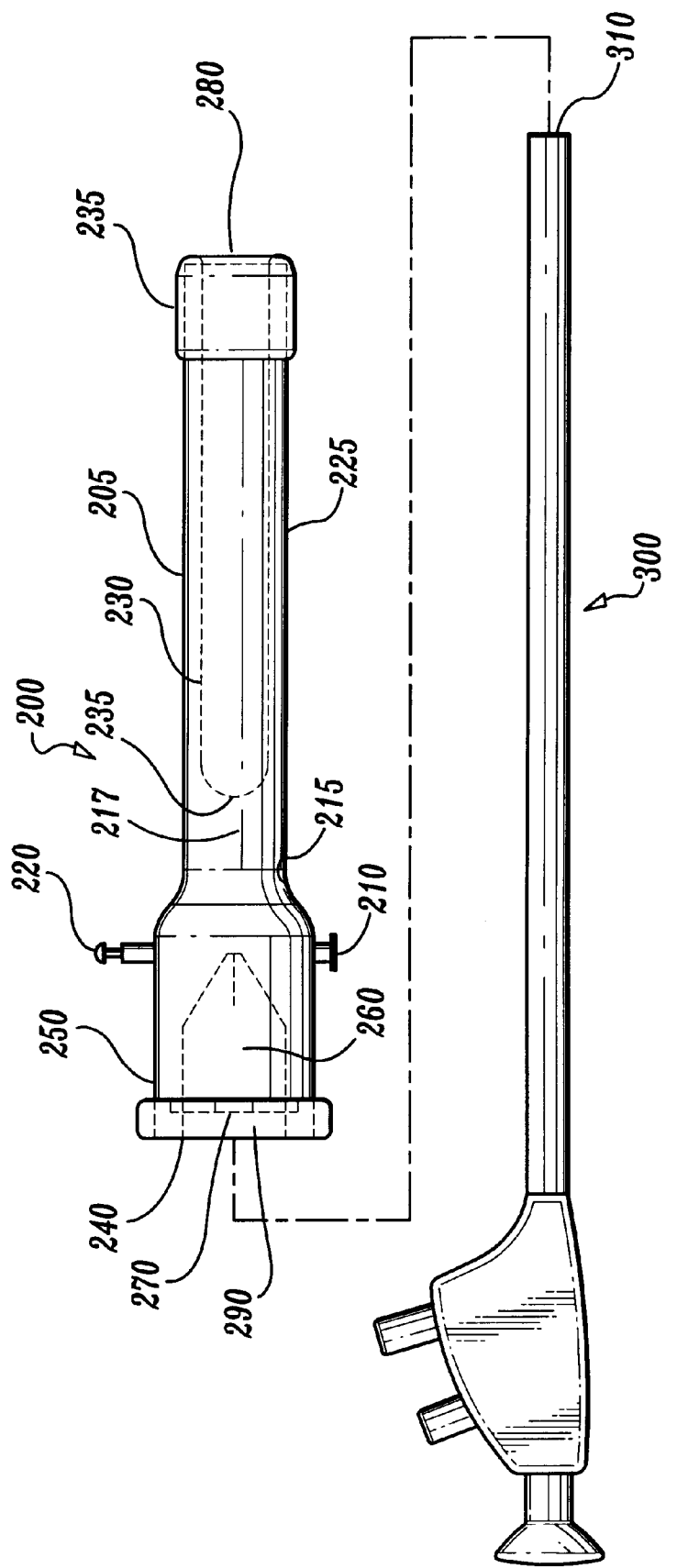
FIG. 22 is a side elevational view of another embodiment of a dissection device with a hollow tube and an inverted balloon attached thereto, the dissection device having a separate endoscope for use therewith.

In another exemplary embodiment illustrated in FIG. 22, a dissection device 200 includes a hollow tube 205, an inflation valve 210, a deflation valve 220, an inverted elongate tubular balloon 230, a valve, such as a duckbill valve 260, to seal the proximal end 250, and a scope seal 270. The hollow tube 205 has an opening 280 on its distal end adapted to receive a scope, an opening 290 on its proximal end and a lumen extending therethrough. The lumen of the hollow tube 205 comprises a luminal surface 215 and a luminal space 217. The inflation valve 210 and deflation valve 220 are in fluid communication with the lumen of the hollow tube 205.

The elongate tubular balloon 280 in its inverted and inflated state is stored within the hollow tube 205. The proximal end 235 of the elongate tubular balloon 230 may be sealed in a fluid-tight manner around the outer wall 225 of the hollow tube 205 at its distal end. Alternatively, the proximal end 235 of the elongate tubular balloon 230 may be sealed in a fluid-tight manner to the luminal surface 215 of the hollow tube 205 or around the outer wall 215 of the hollow tube 205 at its proximal end, such as in FIGS. 8 and 9. The elongate tubular balloon 230 may be multi-chambered such as shown in FIGS. 17, 17A, 17B, 18, 20 and 21. The balloon 230 is preferably formed from a substantially transparent material to facilitate laparoscopic observation through the balloon 230 as described below.

The scope seal 270, which can be made of silicone or other semi-rigid material, may be coupled to the luminal surface 215 of the hollow tube 205, distal to the proximal opening 290 and proximal to the duckbill valve 260. Alternatively, the scope seal 270 may be coupled to the hollow tube 205 by wrapping it around the outer wall 225 of the hollow tube 205 at the proximal end of the hollow tube 205, or sealing it to the proximal end of the hollow tube 205. The duckbill valve 260 can also be made of silicone or other semi-rigid material and may be coupled to the luminal surface 215 of the hollow tube 205 distal to the scope seal 270.

The elongate tubular balloon 230 can be inflated with inflation means such as a syringe or a hand pump in fluid communication with the inflation port 210. During inflation, the elongate tubular balloon 230 everts, propagating distally beyond the distal opening 280 of the hollow tube. The everting balloon 230 dissects tissue as it propagates within the mass of body tissue. Either during inflation or once the elongate tubular balloon 230 is fully inflated, the distal end 310 of the scope 300 can be inserted through the proximal opening 290 of the hollow tube 205, pushed through the scope seal 270 and the duckbill valve 260, and into the inflated elongate tubular balloon 230. With the scope 300, the surgeon can view a blood vessel, such as an IMA, its branches and the connective tissue that is dissected by the elongate tubular balloon 230. Alternatively, the dissection device 200 can be made integrally with the scope 300.

Figure 23:
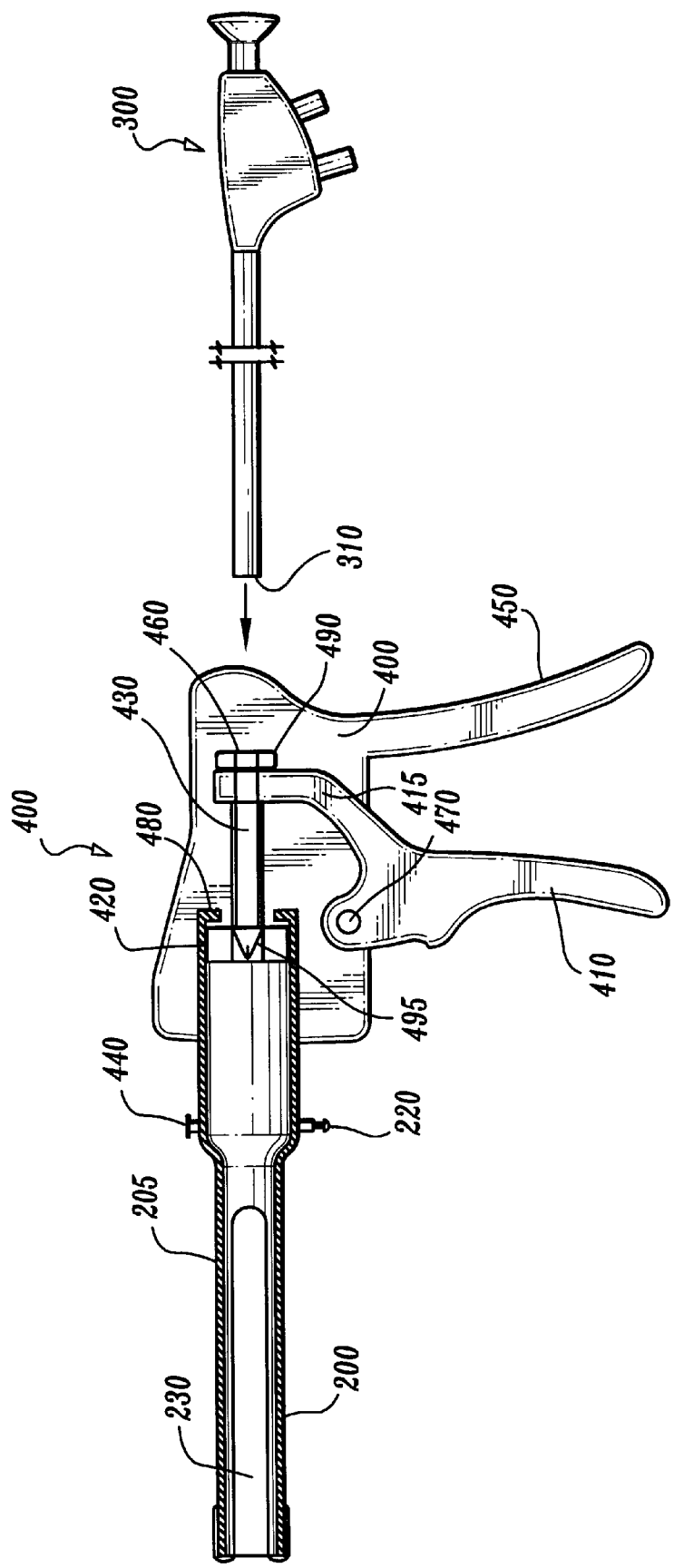
FIG. 23 is a side elevational view of another embodiment of a dissection device with a hand operated inflation pump and separate endoscope for use therewith.

FIG. 23 shows the dissection device of FIG. 22 coupled to a piston pump 400, which is used to inflate the elongate tubular balloon 230. The piston pump 400 comprises a stationary handle 450, a spring actuated trigger 410, a pin 470, a piston rod 430, a piston head 420, piston stops 480, a one-way fluid intake valve 440, and a scope port 460. The trigger 410 is pivotally hinged by hinge 470 to the handle 450. The trigger 410 has an upper arm 415 that is secured to the proximal end of the piston rod 430. The distal end of the piston rod 430 is coupled to the proximal end of the piston head 420. The piston rod 430 has an opening on its proximal end, an opening on its distal end, and a lumen extending therethrough. The piston head 420 has an opening on its proximal end, an opening on its distal end, and a lumen extending therethrough as well. The piston head 420 is secured to the piston rod 430, and the proximal opening of the piston head 420 and the distal opening of the piston rod 430 are in fluid communication.

The elongate tubular balloon 230 is inflated by squeezing the trigger 410, causing the upper arm 415 to pivot distally toward the dissection device 200. The pivoting action of the upper arm 415 forces the piston rod 430 to push the piston head 420 distally, forcing fluid trapped inside the elongate tubular member 205 to inflate the elongate tubular balloon 230. Valving can provide for multiple stroke operation of the pump 400. The elongate tubular balloon 230 can be single chambered as shown in FIGS. 16 and 19 or multi-chambered as shown in FIGS. 17, 17A, 17B, 18, 20, and 21. As the piston head 420 moves distally, the fluid intake valve 440 is closed, thus sealing the inside of the hollow tube 205. The trigger 410 will move back to its original position upon release due to the action of a spring (spring not shown). Thus, the upper arm 415 will move proximally away from the hollow tube 205, pulling the piston rod 430, which in turn pulls the piston head 420 until the piston head rests against the piston stops 480. The distal movement of the piston rod 420 causes a suction effect due to the vacuum inside the lumen of the hollow tube 205, opening the one-way fluid intake valve 440 and allowing fluid to enter the lumen of the hollow tube 205. Thus, the elongate tubular balloon 230 can be inflated with further squeezing and releasing of the trigger 410.

The scope 300 can be inserted into the scope port 460, which has an opening adapted to receive a scope 300 and a scope seal 490. The scope 300 is pushed past the scope seal 490 and through the hollow piston rod 430. A duckbill valve 495, secured to either the distal end of the hollow piston rod 430 or the lumen of the piston head 420, extends into the hollow piston head 420. The scope seal is pushed through the duckbill valve 495 and into the hollow tube 205. This can be done either before inflation, during inflation, or after complete inflation of the elongate tubular balloon 230, because the movement of the scope 300 is independent of the movement of the piston pump 400. Once the elongate tubular balloon 230 is in an inflated and everted state, the scope can be advanced into the everted elongate tubular balloon 230 in order to view a blood vessel, such as an IMA, its branches and the connective tissue that is dissected by the elongate tubular balloon 230. In the case of a multi-chambered elongate tubular balloon 230, the scope can be advanced into whichever chamber is best positioned for viewing a particular area. Finally, the deflation valve 220, can be used to deflate the elongate tubular balloon 230.

The piston pump 400 can either be made integrally with the dissection device 200, or can be made separately and adapted for use with the dissection device 200. Moreover, the piston pump 400 can be made integrally with the scope 300.

Alternatively, the scope 300 can be independently inserted through the same incision in which the dissection device 200 is inserted. The scope 300 can be advanced alongside the everting elongate tubular balloon 230.

Figure 24:
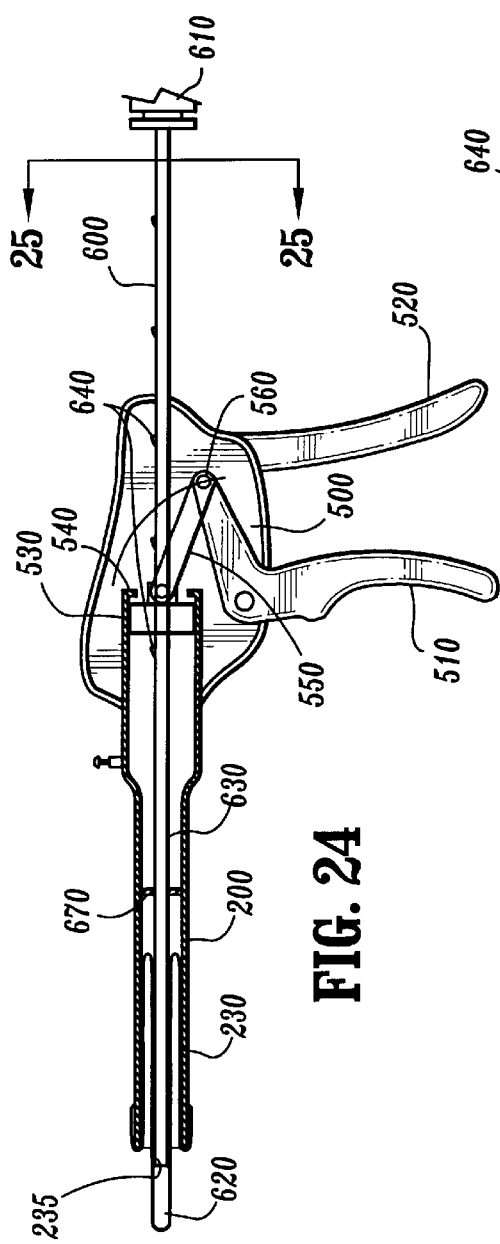
FIG. 24 is a side elevational view of another embodiment of a dissection device having an inverted elongate tubular balloon stored inside of a hollow tube and a longitudinally adjustable guide rod attached to the distal end of the inverted elongate tubular balloon.

In an alternative embodiment, as shown in FIG. 24, the dissection device 200 of FIG. 22 can be used with a piston pump 500 adapted for use with a guide rod 600. The piston pump 500 comprises an L-shaped trigger 510, a handle 520, an upper arm 550, the proximal end of which is attached at an angle to the shoulder of the L-shaped trigger by a pin 560, a piston head 530 and piston stops 540. The piston head 530 has an opening on its proximal end, an opening on its distal end, and a lumen extending therethrough. A guide rod 600 has a handle 610, a blunt end 620, a shaft 630 extending from the handle 610 to the blunt end 620, and multiple triangular piston stops 640 that look like dorsal fins when deployed along the shaft 630. The dissection device 200 has supports 670 to guide the guide rod 600 through the hollow tube 205.

Figure 24A:
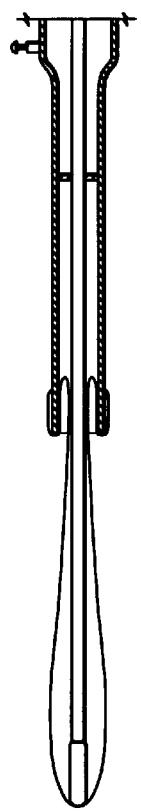
FIG. 24A is a side elevational view of the device of FIG. 24, wherein the guide rod has pushed the uninflated elongate tubular balloon completely out of the hollow tube.

The piston pump 500 inflates the elongate tubular balloon 230 in the same manner as previously described with respect to FIG. 23. The blunt end 620 of the guide rod 600 can be secured to the inverted lumen 235 of the elongate tubular balloon 230 at the distal end of the elongate tubular balloon 230. Thus, the guide rod 600 can be used to retract the elongate tubular balloon 230 after deflation for withdrawal or subsequent use. Alternatively, the guide rod 600 need not be secured to the elongate tubular balloon 230. The guide rod 600 can be pushed manually through the elongate tubular balloon 230, everting the balloon 230 as it propagates along a blood vessel, such as an IMA, as shown in FIGS. 24 and 24a. The guide rod 600 can be pushed either concurrent with or previous to balloon inflation.

Alternatively, the guide rod 600 can be advanced by squeezing the piston pump 500, which will push the piston head 530 distally. The piston head 530 will push against one of the retractable piston stops, thus forcing the guide rod 600 forward. Releasing the trigger 510 will spring the trigger back into its original position (spring not shown), pulling the piston head 530 back against the piston stops 540. The piston head 530 will depress and slide over the piston stops 640 that are in its way, because the piston stops 640 protrude from the shaft 630 of the guide rod 600 at an angle and retract into the shaft 630 when the piston head 530 slides over them from a distal to proximal direction. The shaft 630 can be hollow along its entire length or can have hollow sections in the areas of the piston stops 640 to accommodate for the retraction of the piston stops 640.

Figure 25:
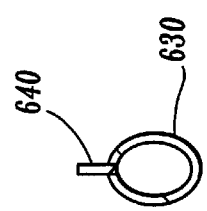
FIG. 25A is a cross-sectional view taken along line 25—25 in FIG. 24, showing a retractable piston stop in an upright, deployed position.
FIG. 25B is an alternative cross-sectional view taken along line 25—25, showing a retractable piston stop in a retracted state.
Figure 25A:
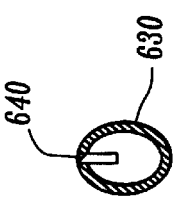
Figure 24B:
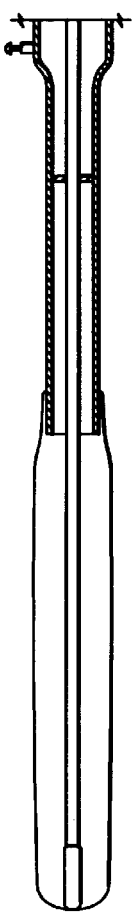
FIG. 24B is a side elevational view of the device of FIG. 24A, wherein the elongate tubular balloon is in a fully inflated state.

FIGS. 25A and 25B show a cross-section through the guide rod 600 and one of the piston stops 640, the piston stop 640 being in an upright, unretracted position in FIG. 25A and a retracted position in FIG. 25B. The retractable piston stops 640 are spaced at distances which will allow the guide rod 600 to advance to a maximum distance at the same time that the elongate tubular balloon 230 is fully inflated, as shown in FIG. 24B. The retractable piston stops 640 are also all retractable at the same time so that the guide rod 600 can be retracted proximally. As indicated in FIG. 24A, the guide rod 600 can be advanced to a maximum distance before the elongate tubular balloon 230 is inflated.

The elongate tubular balloon 230 can have various shapes. It can be multi-chambered as shown in FIGS. 17, 17A, 17B, 18, 20 and 21, in which case, the guide rod 600 could be guided through any one of the chambers. It can also be shorter and have a larger cross-section such as the balloon 800 shown in FIG. 24C or the balloon 700 shown in FIG. 24D. With respect to the balloon 700 shown in FIG. 24D, the hollow tube 710 can be longer to compensate for the shorter length of the balloon 700. Dissection using the guide rod 600, hollow tube 710 and balloon 700 can be carried out by first tunneling with the guide rod 600 and hollow tube 710, followed by inflating the balloon 700, then deflating the balloon, and finally repeating the above steps until dissection along the desired length of a blood vessel, such as an IMA, has been achieved.

Figure 24E:
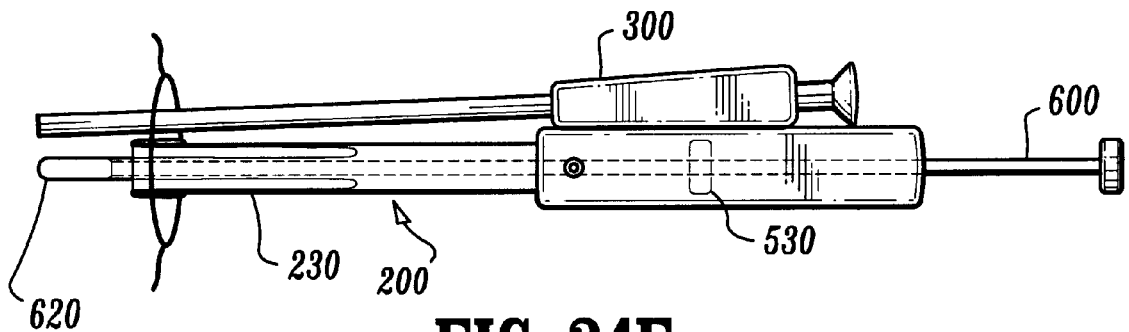
FIG. 24E is a top view of the device depicted in FIG. 24 with separate endoscope used therewith.
Figure 24C:
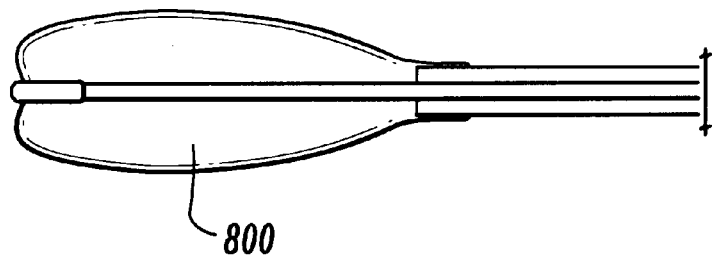
FIGS. 24C and 24D are side elevational views of two more embodiments of the fully inflated elongate tubular balloon depicted in FIG. 24B, wherein the elongate tubular balloons are shorter and have larger diameters than the elongate tubular balloon depicted in FIG. 24B.
Figure 24D:
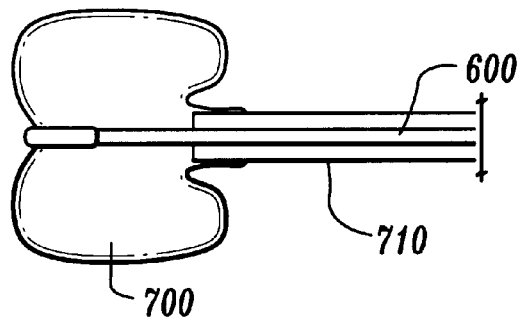

Also, as shown in FIG. 24E, a scope 300 can be inserted through the incision alongside the dissection device 200. With the scope 300, the surgeon can view a blood vessel, such as an IMA, its branches and the connective tissue that is dissected by the blunt end 620 of the guide rod 600 and the elongate tubular balloon 230. It must be appreciated that any openings in the balloon, whether for strings, rods or scopes must be appropriately sealed.

Figures 26, 27:
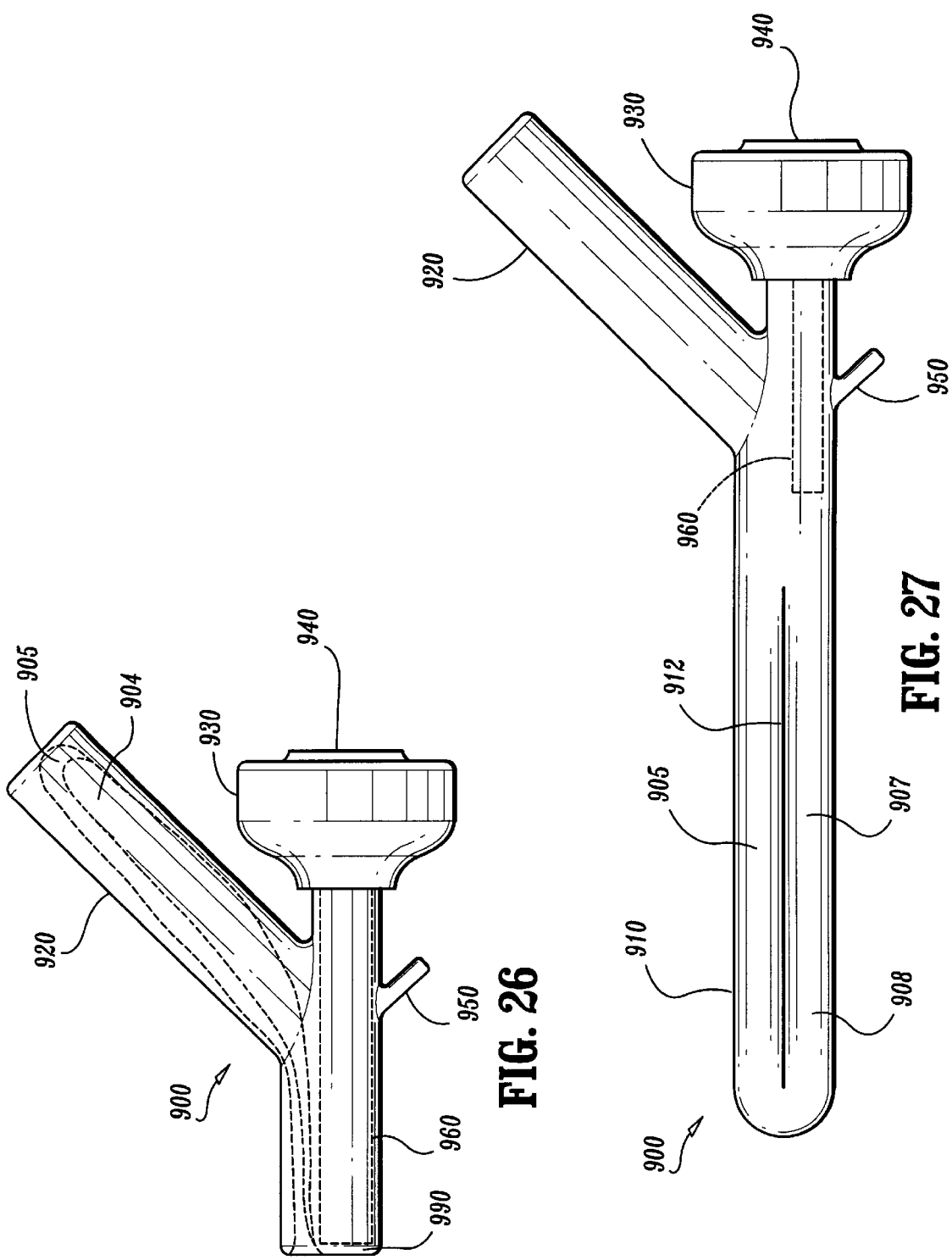
FIG. 26 is a plan view of another embodiment of a dissection device illustrating the storage of the inverted double-chambered elongate tubular balloon of FIG. 13 within a thumb-shaped balloon reservoir.
FIG. 27 is a plan view of the apparatus of FIG. 26 showing the double-chambered elongate tubular balloon fully distended after inflation.

Another exemplary embodiment of a dissection device 900 according to the invention is illustrated in FIGS. 26 and 27. The dissection device 900 is provided with a laterally extending thumb-shaped reservoir 920, which is itself part of the double-chambered elongate tubular balloon 910. A housing 930 having a tubular balloon sleeve 960 extending therefrom terminates the balloon 910 and may receive a laparoscope (not shown) if visualization is required or desirable for the procedure contemplated. An instrument seal 940, which may be of the type described in Fogarty et al., U.S. Pat. No. 5,690,668, is mounted in the housing 930 to provide a fluid-tight seal between the interior of the housing 930, which is in fluid communication with the interior of the double-chambered balloon 910, and a laparoscope. The balloon sleeve 960 may be formed integrally with the housing 930 or as a separate member. The balloon can be inflated through inflation lumen 950, which is in fluid communication with an inflation means (not shown), a dissection device 900 includes a hollow tube 960 and a double-chambered elongate tubular balloon 910 having a laterally extending thumb-shaped reservoir 920.

The double-chambered elongate tubular balloon 910 is substantially similar to the balloons utilized in connection with previous embodiments, such as those illustrated in FIGS. 13, 15A, 15B, and 15C. Thus, elongate tubular balloon 910 in its uninflated state may be inverted with chamber 907 stored inside of chamber 905. The two chambers are separated by weld 912, which may run substantially the entire length of the balloon 910 or the entire length of the balloon 910. If the weld runs the entire length of the balloon, then each chamber may be inflated with its own inflation lumen.

The balloon 910 may further be folded inwardly to reduce its predeployment length as shown in FIG. 27. The proximal end of the balloon 910 is open and may be terminated in a fluid-tight manner in the housing 930, as shown, or on an outer surface of the balloon sleeve 960. The balloon 910 is preferably formed from a substantially transparent material to facilitate laparoscopic observation through the balloon 910.

Prior to use, the deflated balloon 910 is inverted, with chamber 907 being stored in chamber 905, and the distal portion of the balloon 908 is folded inwardly to shorten the overall length of the balloon 910. The distal portion 908 of the inverted, folded balloon 910 is pushed into the reservoir 920, as show in FIG. 27. Additional folds may be provided, as necessary, to further shorten the deflated balloon 910 and to make it possible to store the majority of the balloon 910 in the reservoir 920.

The specificity of the embodiments described is not intended to be limiting as to the scope of the invention.

What is claimed is:

1. A dissection device for dissecting tissue from an elongate structure in a body, the device comprising:
    an elongate tubular member comprising a hollow tube having a wall, a proximal end, a distal end, and a lumen extending therethrough;
    an inflatable elongate tubular balloon having a proximal end, a distal end, a first tubular chamber having a first lumen, and a second tubular chamber having a second lumen, at least a portion of said elongate tubular balloon being inside the hollow tube; and
    means for inflating said elongate tubular balloon.

2. The dissection device of claim 1, wherein said first and second tubular chambers are in fluid communication with each other.

3. The dissection device of claim 2, wherein the proximal end of the elongate tubular balloon has an opening, and wherein the means for inflating the elongate tubular balloon comprises;
    an opening on the wall of the hollow tube; and
    a balloon inflation lumen having a proximal end and a distal end, the proximal end of said lumen including a fitting for connecting to an inflation source and the distal end being in fluid communication with the opening in the proximal end of the elongate tubular balloon.

4. The dissection device of claim 3, wherein the distal end of the inflation lumen is connected to the wall of the hollow tube in a fluid-tight manner, said inflation lumen being in fluid communication with the lumen of the hollow tube.

5. The dissection device of claim 3, wherein the distal end of the inflation lumen is connected to the elongate tubular balloon in a fluid-tight manner.

6. The dissection device of claim 2, wherein the first and second tubular chambers converge at their distal ends into a single distal chamber.

7. The dissection device of claim 2, wherein the first and second tubular chambers converge at their proximal ends into a single proximal chamber.

8. The dissection device of claim 1, wherein the distal end of the hollow tube comprises a flattened opening.

9. The dissection device of claim 1, wherein the distal end of the hollow tube is bent.

10. The dissection device of claim 1, wherein a cross-sectional area of one of said first and said second tubular chambers is larger than a cross-sectional area of the other of said first and said second tubular chambers.

11. The dissection device of claim 1, wherein the means for inflating the elongate tubular balloon comprises;
    an inflation port on the proximal end of the hollow tube;
    a pump in fluid communication with the inflation port; and
    a deflation valve in fluid communication with the first and second tubular chambers of the elongate tubular balloon.

12. The dissection device of claim 1, wherein the proximal end of the elongate tubular member has an opening.

13. The dissection device of claim 12, wherein the proximal end of the elongate tubular balloon is coupled to the distal end of the hollow tube in a fluid-tight manner.

14. The dissection device of claim 12, wherein the proximal end of the elongate tubular balloon is coupled to the lumen of the hollow tube in a fluid-tight manner.

15. The dissection device of claim 12, wherein the proximal end of the elongate tubular balloon is coupled to the proximal end of the hollow tube in a fluid-tight manner.

16. The dissection device of claim 1, wherein at least a portion of the elongate tubular balloon is coated with a lubricant.

17. The dissection device of claim 1, further comprising means for deflating the elongate tubular balloon.

18. The dissection device of claim 1, wherein the first and second tubular chambers are separated by a weld running substantially the length of the elongate tubular balloon.

19. A dissection device for dissecting tissue from an elongate structure in a body, the device comprising:
    an elongate tubular member comprising a hollow tube having a wall, a proximal end, a distal end, and a lumen extending therethrough;
    an inflatable elongate tubular balloon having a proximal end, a distal end, a first tubular chamber having a first lumen, and a second tubular chamber having a second lumen, the elongate tubular balloon in its uninflated state being inverted and stored in the lumen of the hollow tube, said elongate tubular balloon in its inflated state at least partially extending beyond the distal end of the hollow tube; and
    means for inflating the elongate tubular balloon.

20. The dissection device of claim 19, wherein said first and said second tubular chambers are in fluid communication with each other.

21. The dissection device of claim 20, wherein in the uninflated state one of said first and said second tubular chambers of the elongate tubular balloon is inverted while the other of said first and said second tubular chambers is stored in the inverted tubular chamber.

22. The dissection device of claim 21, wherein a cross-sectional area of the inverted tubular chamber is larger than a cross-sectional area of the other tubular chamber.

23. The dissection device of claim 19, wherein the distal end of the hollow tube comprises a flattened opening.

24. The dissection device of claim 19, wherein the distal end of the hollow tube is bent.

25. The dissection device of claim 19, further comprising means for deflating the elongate tubular balloon.

26. The dissection device of claim 20, wherein the first and second tubular chambers are separated by a weld running substantially the length of the elongate tubular member.

27. A dissection device for dissecting tissue from an elongate structure in a body, the device comprising:
   an elongate tubular member comprising a hollow tube having a wall, a proximal end, a distal end, and a lumen extending therethrough;
   an inflatable elongate tubular balloon having a proximal end, a distal end, and multiple tubular chambers, at least a portion of said elongate tubular balloon being inside the hollow tube; and
   means for inflating the elongate tubular balloon.

28. The dissection device of claim 27, wherein the multiple tubular chambers are in fluid communication with each other.

29. The dissection device of claim 28, wherein one of said multiple tubular chambers has a larger cross-sectional area than the others of said multiple tubular chambers.

30. The dissection device of claim 28, wherein the proximal end of the elongate tubular balloon has an opening, and wherein the means for inflating the elongate tubular balloon comprises:
   an opening on the wall of the hollow tube; and
   a balloon inflation lumen having a proximal end and a distal end, the proximal end of said lumen including a fitting for connecting to an inflation source and the distal end being in fluid communication with the opening in the proximal end of the elongate tubular balloon.

31. The dissection device of claim 30, wherein the distal end of the inflation lumen is connected to the wall of the hollow tube in a fluid-tight manner, said inflation lumen being in fluid communication with the lumen of the hollow tube.

32. The dissection device of claim 30, wherein the distal end of the inflation lumen is connected to the elongate tubular balloon in a fluid tight manner.

33. The dissection device of claim 28, wherein the multiple tubular chambers converge at their distal ends into a single distal chamber having a lumen.

34. The dissection device of claim 33, further comprising means for retracting and re-inverting the elongate tubular balloon, said means being coupled to the lumen the single distal chamber of the elongate tubular balloon.

35. The dissection device of claim 28, wherein the multiple tubular chambers converge at their proximal ends into a single proximal chamber having a lumen.

36. The dissection device of claim 27, wherein the distal end of the hollow tube comprises a flattened opening.

37. The dissection device of claim 27, wherein the distal end of the hollow tube is bent.

38. The dissection device of claim 27, wherein the means for inflating the elongate tubular balloon comprises:
   an inflation port on the proximal end of the hollow tube;
   a pump in fluid communication with the inflation port; and
   a deflation valve in fluid communication with the multiple tubular chambers of the elongate tubular balloon.

39. The dissection device of claim 27, wherein the proximal end of the elongate tubular balloon has an opening.

40. The dissection device of claim 39, wherein the proximal end of the elongate tubular balloon is coupled to the distal end of the hollow tube in a fluid-tight manner.

41. The dissection device of claim 39, wherein the proximal end of the elongate tubular balloon is coupled to the lumen of the hollow tube in a fluid-tight manner.

42. The dissection device of claim 39, wherein the proximal end of the elongate tubular balloon is coupled to the proximal end of the hollow tube in a fluid-tight manner.

43. The dissection device of claim 27, wherein at least a portion of the elongate tubular balloon is coated with a lubricant.

44. The dissection device of claim 27, further comprising means for retracting and re-inverting the elongate tubular balloon, said means being coupled to the lumen of one of the multiple chambers of the elongate tubular balloon at the distal end of the elongate tubular balloon.

45. The dissection device of claim 27, further comprising a means for deflating the elongate tubular balloon.

46. The dissection device of claim 27, wherein the elongate tubular balloon has at least two tubular chambers.

47. A dissection device for dissecting tissue from an elongate structure in a body, the device comprising:
   an introducer assembly comprising:
      a hollow housing with a proximal end, a distal end, and lumen therebetween;
      an instrument seal mounted on the proximal end of the housing and in fluid communication with the lumen of the housing; and
      a tubular balloon sleeve with a proximal end and a distal end, the proximal end being connected to the housing;
   an inflatable elongate tubular balloon having a proximal end, a distal end, a laterally extending thumb-shaped reservoir, a first tubular chamber having a first lumen, and a second tubular chamber having a second lumen, the proximal end of the balloon being coupled to the introducer assembly; and
   means for inflating said elongate tubular balloon.

48. The dissection device of claim 47, wherein said first and said second chambers are in fluid communication with each other.

49. The dissection device of claim 48, wherein the first and second tubular chambers converge at their distal ends into a single distal chamber having a lumen.

50. The dissection device of claim 48, wherein the first and second tubular chambers converge at their proximal ends into a single proximal chamber having a lumen.

51. The dissection device of claim 47, wherein the means for inflating the elongate tubular balloon comprises a balloon inflation lumen having a proximal end and a distal end, the proximal end of said lumen including a fitting for connecting to an inflation source and the distal end being in fluid communication with at least one of the said first and said second tubular chambers of the elongate tubular balloon.

52. The dissection device of claim 47, wherein the proximal end of the elongate tubular balloon is secured to the introducer assembly in a fluid-tight manner.

53. The dissection device of claim 52, wherein the proximal end of the elongate tubular balloon terminates at the balloon sleeve and is sealed around the balloon sleeve in a fluid-tight manner.

54. The dissection device of claim 52, wherein the proximal end of the elongate tubular balloon terminates at the housing and is sealed to the housing in a fluid-tight manner.

55. The dissection device of claim 52, wherein the proximal end of the elongate tubular balloon is secured to the introducer assembly between the lumen of the housing and the balloon sleeve.

56. The dissection device of claim 47, wherein at least a portion of the elongate tubular balloon is coated in a lubricant.

57. The dissection device of claim 47, wherein the elongate tubular balloon is formed of a substantially transparent material.

58. The dissection device of claim 47, wherein in the uninflated state one of said first and said second tubular chamber of the elongate tubular balloon is inverted while the other of said first and said second tubular chambers is stored in the inverted tubular chamber.

59. The dissection device of claim 58, wherein a cross-sectional area of the inverted tubular chamber is larger than a cross-sectional area of the other tubular chamber.

60. The dissection device of claim 47, wherein the distal end of the elongate tubular balloon has a fully inflated length greater than the length of the introducer assembly.

61. The dissection device of claim 60, wherein in the uninflated state, the distal end of the elongate tubular member is stored inside the thumb-shaped reservoir.

62. The dissection device of claim 47, further comprising a scope with a proximal end and a distal end, the distal end being inserted through the instrument seal of the introducer assembly.

* * * * *